(12) United States Patent
Manoharan

(10) Patent No.: US 6,525,031 B2
(45) Date of Patent: Feb. 25, 2003

(54) TARGETED OLIGONUCLEOTIDE CONJUGATES

(75) Inventor: Muthiah Manoharan, Carlsbad, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/934,424

(22) Filed: Aug. 21, 2001

(65) Prior Publication Data

US 2002/0058639 A1 May 16, 2002

Related U.S. Application Data

(62) Division of application No. 09/097,753, filed on Jun. 16, 1998, now Pat. No. 6,300,319.

(51) Int. Cl.[7] .......................... C12Q 1/68; A01N 61/00; A01N 43/04; C07H 19/00; C07H 21/00
(52) U.S. Cl. .................... 514/44; 514/1; 435/6; 536/22.1; 536/23.1; 536/24.5; 536/25.3
(58) Field of Search .................... 435/6; 514/1, 44; 536/22.1, 23.1, 24.5, 25.3

(56) References Cited

U.S. PATENT DOCUMENTS

| | | | |
|---|---|---|---|
| 5,108,921 A | 4/1992 | Low et al. | 435/240.1 |
| 5,138,045 A | 8/1992 | Cook et al. | 536/27 |
| 5,212,295 A | 5/1993 | Cook | 536/26.7 |
| 5,218,105 A | 6/1993 | Cook et al. | 536/25.31 |
| 5,378,825 A | 1/1995 | Cook et al. | 536/25.34 |
| 5,386,023 A | 1/1995 | Sanghvi et al. | 536/25.3 |
| 5,416,016 A | 5/1995 | Low et al. | 435/240.1 |
| 5,457,191 A | 10/1995 | Cook et al. | 536/27.13 |
| 5,459,255 A | 10/1995 | Cook et al. | 536/27.13 |
| 5,506,351 A | 4/1996 | McGee | 536/55.3 |
| 5,521,302 A | 5/1996 | Cook | 536/25.31 |
| 5,539,082 A | 7/1996 | Nielsen et al. | 530/300 |
| 5,541,307 A | 7/1996 | Cook et al. | 536/23.1 |
| 5,554,746 A | 9/1996 | Ravikumar et al. | 540/200 |
| 5,571,902 A | 11/1996 | Ravikumar et al. | 536/22.1 |
| 5,578,718 A | 11/1996 | Cook et al. | 536/27.21 |
| 5,587,361 A | 12/1996 | Cook et al. | 514/44 |
| 5,587,469 A | 12/1996 | Cook et al. | 536/23.1 |
| 5,587,470 A | 12/1996 | Cook et al. | 536/23.1 |
| 5,599,797 A | 2/1997 | Cook et al. | 514/44 |
| 5,602,240 A | 2/1997 | De Mesmaeker et al. | 536/22.1 |
| 5,608,046 A | 3/1997 | Cook et al. | 536/24.5 |
| 5,610,289 A | 3/1997 | Cook et al. | 536/25.34 |
| 5,955,365 A * | 9/1999 | Szoka et al. | 435/441 |

FOREIGN PATENT DOCUMENTS

WO   WO 86/02929   5/1986

OTHER PUBLICATIONS

Letsinger et al. PNAS, vol. 86, pp. 6553–6556, 1989.*

Agrawal, et al., "Olidogeoxynucleoside phosphoramidates and phosphorothioates as inhibitors of human immunodeficiency virus", *Proc. Natl. Acad. Sci.*, 1988, 85, 7079–7083.

Akhtar, et al., "Interactions of antisense DNA oligonucleotide analogs with phospolipid membranes (liposomes)", *Nucleic Acids Res.*, 1991, 19, 5551–5559.

Ashwell, G. and Harford, J., "Carbohydrate–Specific Receptors of the Liver", *Ann. Rev. Biochem.*, 1982, 51, 531–554.

Asseline, et al., "Nucleic acid–binding molecules with high affinity and base sequence specificity: Intercalating agents covalently linked to oligodeoxynucleotides", *Proc. Natl. Acad. Sci. USA*, 1984, 81, 3297–3301.

Azad, et al., "Antiviral Activity of a Phsophorothioate Oligonucleotide Complementary to RNA of the HumanCytomegalovirus Major Immediate–Early Region", *Antimicrob. Agents Chemother.*, 1993, 37, 1945–1954.

Bayer, et al., "Improved Conditions for Soldi Phase Synthesis of Oligonucleotides on PS–PEG Copolymers", *Z. Naturforsch*, 1995, 50B, 1096–1100.

Beaucage, et al., "Advances in the Synthesis of Oligonucleotides by the Phosphoramidite Approach", *Tetrahedron*, 1992, 48, 2223–2311.

Bennett, et al., "Cationic Lipids Enhance Cellular Uptake and Activity of Phosphorothioate Antisense Oligonucleotides", *Mol. Pharmacol.*, 1992, 41, 1023–1033.

Betebenner, et al., "Hepatobiliary Delivery of Polyaminopolycarboxylate Chelates: Synthesis and Characterization of a Cholic Acid Conjugate of EDTA and Biodistribution and Imaging Studies witn Its Indium–111 Chelate", *Bioconjugate Chem.*, 1991, 2, 117–123.

Bevilacqua, et al., "Endothelial Leukocyte Adhesion Molecular 1: An Inducible Receptor for Neutrophils Related to Complement Regulatory Proteins and Lectins", *Science*, 1989, 243, 1160–1165.

Biessen, et al., "Synthesis of Cluster Galactosides with High Affinity for the Hepatic Asialoglycoprotein Receptor", *J. Med. Chem.*, 1995, 38, 1538–1546.

Birchenall–Roberts, et al., "Inhibiton of Murine Monocyte Proliferation by a Colony–Stimulating Factro–1 Antisense Oligodeoxynucleotide", *J. Immunol.*, 1990, 145, 3290–3296.

Bonfils, et al., "Uptake by macrophages of a biotinylated oligo–α–deoxythymidylate by using mannosylated streptavidin", *Bioconjugate*, 1922, 3, 277–284.

(List continued on next page.)

*Primary Examiner*—Jezia Riley
(74) *Attorney, Agent, or Firm*—Woodcock Washburn LLP

(57) ABSTRACT

The present invention provides improved ingress of therapeutic and other moieties into cellular targets. In accordance with preferred embodiments, complexes are provided which carry primary moieties, chiefly therapeutic moieties, to such target cells. Such complexes preferably feature cell surface receptor ligands to provide specificity. Such ligands are preferably bound to primary moieties through polyfunctional manifold compounds.

22 Claims, No Drawings

OTHER PUBLICATIONS

Boutorin, et al., "Synthesis of akylating oligonucletide derivatives containing cholesterol or phenazinium residues at their 3+–terminus and their interaction with DNA within mammalian cells", *FEBS Lett.*, 1989, 254, 129–132.

Breitfeld, et al., "Cell Biology of the Asialoglycoprotein Receptor System: A Model of Receptor–Mediated Endocytosis", *Int. Rev. Cytol.*, 1985, 97, 47–95.

Brinkley, M., "A Brief Survey of Methods for Preparing Protein conjugates with Dyes Haptens, and Cross–Linking Reagents", *Bioconjugate Chem.*, 1992, 3, 2–13.

Bunnel, et al., "Targeted Delivery of Antisense Oligonucleotides by Molecular Conjugates", *Somatic Cell Molecular Genetics*, 1992, 18, 559–569.

Chiu, et al., "In Vivo Targeting Function of N–Linked Oligosaccharides with Terminating Galactose and N–Acetylgalactosamine Residues", *J. Biol. Chem.*, 1994, 269, 16195–16202.

Chollet, "Selective Attachment of Oligonucleotides to Interleukin 1β and Taargeted Delivery to Cells", *Nucleosides & Nucleotides*, 1990, 9, 957–966.

Citro, et al., "Inhibition of leukemia cell proliferation by folic acid–polylysine–mediated introduction of c–myb antisense oligodeoxynucleotides into HL–60 cells", *Br. J. Cancer*, 1992, 69, 463–467.

Citro, et al., "Inhibition of leukemia cell proliferation by receptor–mediated uptake of c–myb antisenseoligodeoxynucleotides", *Proc. Natl. Acad. Sci.*, 1992, 89, 7031–7035.

Corey, et al., "Generation of a Hybrid Sequence–Specific Single–Stranded Deoxyribonuclease", *Science*, 1987, 238, 1401–1403.

Corey, et al., "Sequence–Selective Hydrolysis of Duplex DNA by and Oligonucleotide–Directed Nuclease", *J. Am. Chem. Soc.*, 1989, 111, 8523–8525.

Coste, et al., "Coupling N–Methylated Amino Acids Using PyBroP[1] and PyCloP Halogenophosphonium Salts: Mechanism and Fields of Application", *J. Org. Chem.*, 1994, 59, 2437–2446.

Manoharan, M., "Designer Antisense Oligonucleotides: Conjugation Chemistry and Functionality Placement", S.T. Crooke and B. Lebleu, Eds., *Antisense Research and Applications*, CRC Press, Boca Raton, FL, 1993, pp. 303–349.

Curtis, et al., "Sequence and expression of a membrane–associated C–type lectin that exhibits CD4–independent binding of human immunodeficiency virusenvelope glycoprotein gp120", *Proc. Natl. Acad. Sci.*, 1992, 89, 8356–8360.

Dreyer, et al., "Sequence–specific cleavage of single–stranded DNA: Oligodeoxynucleotide–EDTA•FE(II)", *Proc. Natl. Acad. Sci USA*, 1985, 82, 968–972.

Drickamer, K., "Two Distinct Classes of Carbohydrate–recognition Domains in Animal Lectins", *J. Biol. Chem.*, 1988, 263, 9557–9560.

Drickamer, K., "$CA^{2+}$ dependent carbohydrate–recognition domains in animal proteins", *Curr. Opin. Struct. Biol.*, 1993, 3, 393–400.

Drickamer, K., "Recognition of complex carbohydrates by $CA^{2+}$–dependent animal lectins", *Biochem. Soc. Trans.*, 1993, 21, 456–459.

Drickamer, K., "Clearing Up Glycoprotien Hormones", *Cell*, 1991, 67, 1029–1032.

Duncan, R., "Drug–polymer conjugates: potential for improved chemotherapy", *Anticancer Drugs*, 1992, 3, 175–210.

Edelman, G.M., "Cell Adhesion and the Molecular Processes of Morphogenesis", *Annu. Rev. Biochem.*, 1985, 54, 135–168.

Farhood, et al., "Cationic Liposomes for Direct Gene Transfer in Therapy of Cancer and Other Diseases", *N.Y. Acad. Sci.*, 1994, 716, 23–35.

Felgner, et al., "Particulate systems and polymers for in vitro and in vivo delivery of polynucleotides", *Adv. Drug. Deliv. Res.*, 1990, 5, 163–187.

Florman, H.M., "O–Linked Oligosaccharides of Mouse Egg ZP3 Account for Its Sperm Receptor Activity", *Cell*, 1985, 41, 313–324.

Freier, et al., "The ups and downs of nucleic acid duplex stability: structure–stability studies on chemically–modified DNA; RNA duplexes", *Nucleic Acids Res.*, 1997, 25, 4429–4443.

Goldstein, et al., "Evidence of coexistence of dopamine and CCK in meso–limbic neurones" *Nature*, 1980, 285, 476–478.

Gordon, et al., "Macrophage Plasma Membrane Receptors: Structure and Function", *J. Cell. Sci. Suppl.*, 1988, 9, 1–26.

Haensler, et al., "Synthesis and Characterization of a Trigalactosylated Bisacridine Compound to Target DNA to Hepatocytes", *Bioconjugate Chem.*, 1993, 4, 85–93.

Haralambidis, et al., "The Solid Phase Synthesis of Oligonucleotides Containing a 3'–Peptide Moeity", *Tetrahedron Letters*, 1987, 28, 5199–5202.

Haralambidis, et al., "Preparation of Base–modified nucleosides suitable for non–radioactive label attachment and their incorporation into synthetic oligodeoxyribonucleotides", *Nucleic Acid Research*, 1987, 15, 4857–4876.

Hayashi, et al., "Artificial Protein–Protein Complexation between a Reconstituted Myoglobin and Cytochrome c", *J. Am. Chem. Soc.*, 1988, 120, 4910–4915.

Hook, "Cell–Surface Glycosaminoglycans", *Annu. Rev. Biochem.*, 1984, 53, 847–869.

Hoyle, et al., "Molecular Cloning and Sequencing of a cDNA for a Carbohydrate Binding Receptor Unique to Rat Kupffer Cells", *J. Biol. Chem.*, 1988, 263, 7487–7492.

Huang, et al., "pH–Sensitive Immunoliposomes", *Methods Enzymol.*, 1987, 149, 88–99.

Ii, et al., "Molecular Cloning and Sequence Analysis of cDNA Encoding the Macrophage Lectin Specific for Galactose and N–Acetylgalactosamine", *J. Biol. Chem.*, 1990, 265, 11295–11298.

Cline and Hanna, "The Aminolysis of N–Hydroxysuccinimide Esters. A Structure–Reactivity Study", *J. Am. Chem. Soc.*, 1987, 109, 3087–3097.

Jaskulski, et al., "Inhibition of Cellular Proliferation by Antisense Oligodeoxynucleotides to PCNA Cyclin", *Science*, 1988, 240, 1544–1546.

Johnston, et al., "Cloning of GMP–140, a Granule Membrane Protein of Platelets and Endothelium: Sequence Similarity to Proteins Involved in Cell Adhesion and Inflammation", *Cell*, 1989, 56, 1033–1044.

Juby, et al., "Facile Preparation of 3'–Oligonucleotide–Peptide Conjugates", *Tetrahedron Letters*, 1991, 32, 879–882.

Karlsson, et al., "Glycobiology: a growing field for drug design", *TIPS*, 1991, 12, 265–272.

Kawaguchi, et al., "Differential Uptake of D–Galactosyl-and D–Glucosyl–neoglycoproteins by Isolated Rat Hepatocytes", *J. Biol. Chem.*, 1981, 256, 2230–2234.

Kikutani, et al., "Molecular Structure of Human Lymphocyte Receptor for Immunoglobulin E", *Cell*, 1986, 47, 657–665.

Kumar, et al., "Improved Method for 3'–O–Succinylation of 2'–Deoxyribo–and Ribo–Nucleosides and Their Covalent Anchoring on Polymer Supports for Oligonucleotide Synthesis", *Nucleosides and Nucleotides*, 1993, 12, 565–584.

Krieg, et al., "Uptake of Oligodeoxyribonucleotides by Lymphoid Cells is Heterogenous", *Antisense Res. And Dev.*, 1991, 1, 161–171.

Laskyk, et al., "Cloning of a Lymphocyte Homing Receptor Reveals a Lectin Domain", *Cell*, 1989, 56, 1045–1055.

Lee, R.T. and Lee, Y.C., "Effect of Amphiphilic Model Peptides on Biomembranes and Mast Cells", *Glyconconjugate, J.*, 1987, 4, 317–320.

Lee, et al., "Binding of Synthetic Oligosaccharides to the Hepatic Gal/GalNAc Lectin", *J. Biol. Chem.*, 1983, 258, 199–202.

Lemaitre, et al., "Specific antiviral activity of a poly(L–l-ysine)–conjugated oligodeoxyribonucleotide sequence complementary to vesicular stomatitis virus N protein mRNA initiation site", *Proc. Natl. Acad. Sci.*, 1987, 84, 648–652.

Leonetti, et al., "Antiviral activity of conjugates between poly(L–lysine) and synthetic oligodeoxyribonucleotides", *Gene*, 1988, 72, 323–332.

Leonetti, et al., "Antibody–targeted liposomes containing oligodeoxyribonucleotides complementary to viral RNA selectively inhibit viral replication", *Proc. Natl. Acad. Sci.*, 1990, 87, 2448–2451.

Letsinger, et al., "Cholesterol–conjugated oligonucleotides; Synthsis, properties and activity as inhibiors of replication of human immunodeficiency virus in cell culture", *Proc. Natl. Acad. Sci.*, 1989, 86, 6553–6556.

Matsukura, et al., "Phosphorothioate analogs of oligodeoxynucleotides: Inhibitors of replication and cytopathic effects of human immunodeficiency virus", *Proc. Natl. Acad. Sci.*, 1987, 84, 7706–7710.

Miller, et al., "Control of ribonucleic acid function by oligonucleoside methylphosphonates", *Biochemie*, 1985, 67, 769–776.

Miller, et al., "Biochemical and Biological Effects of Nonionic Nucleic Acid Methylphosphonates", *Biochemistry*, 1981, 20, 1874–1880.

Moleman, et al., "Targeting of Antiviral Drugs to $T_4$–Lymphocytes—Anti–HIV Activity of Neoglycoprotein–Aztmp Conjugates In Vitro", *Biochem. Pharmacol.*, 1990, 40, 2603–2610.

Monsigny, et al., "Endogenous Lectins and Drug Targeting", *N.Y. Acad. Sci.*, 1988, 551, 399–414.

Morgan, et al., "Effects of synthetic polycations on leucine incorporation, lactate dehydrogenase release, and morphology of human umbilical vein endothelial cells", *J. Cell. Sci.*, 1988, 91, 231–238.

Nelson, et al., "Bifunctional oligonucleotide probes synthesized using a novel CPG: support are able to detect single base pair mutations", *Nucl. Acids Res.*, 1989, 17, 7187–7195.

Plank, et al., "Gene Transfer into Hepatocytes Using Asialoglycoprotein Receptor Mediated Endocytosis of DNA Complexed with an Artificial Tetra–Antennary Galactose Ligand", *Bioconjugate Chem.*, 1992, 3, 533–539.

Reinis, et al., "Receptor–mediated transport of oligodeoxynucleotides into hepatic cells", *J. Virol. Meth.*, 1993, 42, 99–105.

Scharenberg, et al., "Expression of Deoxyadenosine and Deoxyguanosine Toxicity at Different Stages of Lymphocyte Activation", *J. Immunol.*, 1988, 28, 87–93.

Schwartz, A.L., "The Hepatic Asialoglycoprotein Receptor", *CRC Crit. Rev. Biochem.*, 1984, 16, 207–233.

Seymour, L.W., "Passive Tumor Targeting of Soluble Macromolecules and Drug Conjugates", *Crit. Rev. Ther. Drug Carrier Syst.*, 1992, 9, 135–187.

Shea, et al., "Synthesis, hybridization properties and antiviral activity of lipid–oligodeoxynucleotide conjugates", *Nucleic Acids Res.*, 1990, 18, 3777–3783.

Shen, et al., "Saccharide Determinants in Selective Drug, Delivery,", *Annals N.Y. Acad. Sci.*, 1987, 507, 272–280.

Sidi, et al., "Differential metabolism of deoxyribonucleosides by leukaemic T cells of immature and mature phenotype", *Br. J. Haematol*, 1985, 61, 125–134.

Smith, et al., "Antiviral effect of an oligo(nucleoside methylphosphonate) complementary to the splice junction of herpes simplex virus type 1 immediate early re–mRNAs 4 and 5", *Proc. Natl. Acad. Sci.*, 1986, 83, 2787–2791.

Spellman, "Carbohydrate Characterization of Recombinant Glycoproteins of Pharmaceutical Interest", *Anal. Chem.*, 1990, 62, 1714–1722.

Spiess, et al., "Sequence of Human Asialoglycoprotein Receptor cDNA", *J. Biol. Chem.*, 1985, 260, 1979–1982.

Stevenson, et al., "Inhibition of Human Immunodeficiency Virus Type 1–mediated Cytopathic Effects by Poly(L–lysine)–conjugated Synthetic Antisense Oligodeoxyribonucleotides", *J. Gen. Virol.*, 1989, 70, 2673–2682.

Sullivan, et al., "Inhibition of Human Immunodeficiency Virus–1 Proliferation by Liposome–Encapsulated Sense DNA to the 5' TAT Splice Acceptor Site", *Antisense Res. Devel.*, 1992, 2, 187–197.

Tamura, et al., "Reducing–End Modification of N–Linked Oligosaccharides with Tyrosine", *Anal. Biochem.*, 1994, 216, 335–344.

Taylor, et al., "Contribution to Ligand Binding by Multiple Carbohydrate–recognition Domains in the Macrophage Mannose Receptor", *J. Biol Chem.*, 1992, 267, 1719–1726.

Telser, et al., "Synthesis and Characterization of DNA Oligomers and Duplexes Containing Covalently Attached Molecular Label Comparison of Biotin, Fluorescein, and Pyrene Labels by Thermodynamic and Optical Spectroscopic Measurements", *J. Am. Chem. Soc.*, 1989, 111, 6966–6976.

Tortora, et al., "An Antisense Oligodeoxynucleotide targeted against the type $II_\beta$ regulatory subunit mRNA of protein kinase inhibits cAMP–induced differentiation in HL–60 leukemia cells without affecting phorbol ester effects", Proc. Acad. Sci., 1990, 87, 705–708.

Tropper, et al., "Phase Transfer Catalysis as a General and Stereoselective Entry into Glycosyl Azides Glycosyl Halides", *Synthesis*, 1992, 7, 618–620.

Tropper, et al., "New Methods in Glycoconjugate Synthesis", Thesis, University of Ottawa, 1992.

Ueki, et al., "The Structure of Ancovenin, A New Peptide Inhibitor of Angiotensin I Converting Enzyme", *Tetrahedron Lett.,* 1985, 26, 665–668.

Van Den Hamer, et al., "Physical and Chemical Studies on Ceruloplasmin", *J. Mol. Biol.,* 1970, 245, 4397–4402.

Vickers, et al., "Rational screening of oligonucleotide combinatorial libraries for drug discovery", *Nucleic Acids Res.,* 1993, 21, 1853–1856.

Wickstrom, et al., "Human promyelocytic leukemia HL–60 cell proliferation and c–myc protein expression are inhibited by an antisense pentadecadeoxynucleotide targeted against c–myc mRNA", *Proc. Natl. Acad. Sci.,* 1988, 85, 1028–1032.

Wistler and Wollfrom, Eds., Methods in Carbohydrate Chemistry, Academic Press, New York, 1962, vol. 1–6.

Wu–Pong, et al., "Antisense c–myc Oligodeoxyribonucleotide Cellular Uptake", *Pharm. Res.,* 1992, 9, 1010–1017.

Wu, G.Y. and Wu, C.H., "Specific Inhibition of Hepatitis B Viral Gene Expression in Vitro by Targeted Antisense Oligonucleotides", *J. Biol. Chem.,* 1992, 267, 12436–12439.

Yamada, K.M.,, "Cell Surface Interactions with Extracellular Materials", *Annu. Rev. Biochem.,* 1983, 52, 761–799.

Zerial, et al., "Selective inhibition of the cytopathic effect of type A infleunza viruses by oligodeoxynucleotides covalently linked to an intercalating agent", *Nucleic Acids Res.,* 1987, 15, 9909–9919.

Zuckermann, et al., "Site–Selective Cleavage of RNA by a Hybrid Enzyme", *J. Am. Chem. Soc.,* 1988, 110, 1614–1615.

* cited by examiner

TARGETED OLIGONUCLEOTIDE CONJUGATES

This application is a divisional of application Ser. No. 09/097,753 filed Jun. 16, 1998 now U.S. Pat. No. 6,300,319.

FIELD OF THE INVENTION

The present invention relates to complex compounds and methods for using such complex compounds. The compounds of the invention are preferably used in methods for targeting cellular receptors that facilitate endocytic processes. The present invention takes advantage of this receptor targeting to enhance the intracellular uptake of biologically active compounds for therapeutic purposes.

BACKGROUND OF THE INVENTION

The use of synthetic, short, single stranded oligonucleotide sequences to inhibit gene expression has evolved to the clinical stage in humans. It has been demonstrated that incorporation of chemically modified nucleoside monomers into oligonucleotides can produce antisense sequences which can form more stable duplexes and can have high selectivity towards RNA (Frier et al., *Nucleic Acids Research*, 1997, 25, 4429–4443). Two modifications that have routinely given high binding affinity together with high nuclease resistance are phosphorothioates and methylphosphonates.

There are a number of desirable properties such as specificity, affinity and nuclease resistance that oligonucleotides should possess in order to elicit good antisense activity. The ability to selectively target and be taken up by diseased cells is another important property that is desirable in therapeutic oligonucleotides. Natural oligonucleotides are polyanionic and are known to penetrate cells at very low concentrations. Neutral oligonucleotides, such as the methylphosphonates, are taken up by cells at much higher concentrations. Although the processes by which antisense oligonucleotides enter the cell membrane are not well understood, there is substantial evidence for distinct mechanisms of cell entry based on the electronic character of the antisense sequence.

Delivery of an antisense oligonucleotide to a specific, diseased cell is a very important area of active research. The majority of projected antisense therapies are for viral infections, inflammatory and genetic disorders, cardiovascular and autoimmune diseases and significantly, cancer. For example, in conventional chemotherapy, neoplasticity and virus-related infections are treated with high drug concentrations, leading to overall high systemic toxicity. This method of treatment does not distinguish between diseased cells and healthy ones.

In the treatment of cancers, the ability of antisense agents to down-regulate or inhibit the expression of oncogenes involved in tumor-transforming cells has been well documented in culture and animal models. For example, antisense inhibition of various expressed oncogenes has been demonstrated in mononuclear cells (Tortora et al., *Proc. Natl. Acad. Sci.*, 1990, 87, 705), in T-cells, in endothelial cells (Miller et al., P.O.P., *Biochimie*, 1985, 67, 769), in monocytes (Birchenall-Roberts et al., *Suppl.* 1989, 13 (P.t. C), 18), in reticulocytes (Jaskulski, et al., *Science* 1988, 240, 1544) and in many other cell types, as generally set forth in Table 1.

TABLE 1

INHIBITION OF MAMMALIAN GENE EXPRESSION

| INHIBITION OF EXPRESSION | CELL TYPE |
|---|---|
| T cell receptor | T cells |
| Colony-stimulating factors | Endothelial cells |
| β-Globin | Reticulocytes |
| Multiple drug resistance | MCF-1 cells |
| cAMP kinase | HL-60 cells |
| bcl-2 | L697 cells |
| c-myb | Mononuclear cells |
| c-myc | T-lymphocytes |
| Interleukins | Monocytes |

Virally infected cell cultures and studies in animal models have demonstrated the great promise of antisense and other oligonucleotide therapeutic agents. Exemplary targets from such therapy include eukaryotic cells infected by human immunodeficiency viruses (Matsukura et al., *Proc. Natl. Acad. Sci.*, 1987, 84, 7706; Agrawal et al., *Proc. Natl. Acad. Sci.*, 1988, 85, 7079), by herpes simplex viruses (Smith et al., P.O.P., *Proc. Natl. Acad. Sci.*, 1986, 83, 2787), by influenza viruses (Zerial et al., *Nucleic Acids Res.*, 1987, 15, 9909) and by the human cytomegalovirus (Azad et al., *Antimicrob. Agents Chemother.*, 1993, 37, 1945). Many other therapeutic targets also are amenable to such therapeutic protocols.

The use of non-targeted drugs, to treat disease routinely causes undesirable interactions with non-diseased cells (Sidi et al., *Br. J. Haematol.*, 1985, 61, 125; Scharenberg et al., *J. Immunol.*, 1988, 28, 87; Vickers et al., *Nucleic Acids Res.*, 1991, 19, 3359; Ecker et al., *Nucleic Acids Res.*, 1993, 21, 1853). One example of this effect is seen with the administration of antisense oligonucleotide in hematopoietic cell cultures that exhibit non-specific toxicity due to degradative by-products.

Other research efforts suggest that antisense oligonucleotides possess more side effects in both in vitro and in vivo animal models. For example, non-complementary DNA sequences have been shown to interfere with cell proliferation and viral replication events through unknown mechanisms of action (Kitajima ibid). This reinforces the desirability of oligonucleotides that are specifically targeted to diseased cells.

When phosphodiester oligonucleotides are administered to cell cultures, a concentration of typically about 1 mmol is required to see antisense effects. This is expected since local endonucleases and exonucleases cleave these strands effectively and only 1–2% of the total oligonucleotide concentration becomes cell-associated (Wickstorm et al., *Proc. Natl. Acad. Sci.* 1988, 85, 1028; Wu-Pong et al., *Pharm. Res.* 1992, 9, 1010). If chemically modified oligonucleotides, such as the phosphorothioates or methylphosphonates are used, the observed antisense effects are anywhere between 1 and 100 $\mu$M. This observed activity is primarily due to the relatively slow cellular uptake of oligonucleotides. There is evidence which suggests that a 80 kiloDalton (kDa) membrane receptor mediates the endocytic uptake of natural and phosphorothioate oligonucleotides in certain type of cells. Other data question the existence of such a link between receptor-mediated oligonucleotide uptake and internalization of oligonucleotides. For example, inhibitors of receptor-mediated endocytosis have no effect on the amount of oligonucleotide internalized in Rauscher cells (Wu-Pong et al., *Pharm. Res.*, 1992, 9, 1010). For uncharged methylphosphonates, it was previously believed that internalization of such agents occurred by passive diffusion (Miller et al., *Biochemistry* 1981, 20, 1874). These findings were disproved by studies showing that methylphosphonates take up to 4 days to cross phospholipid bilayers, which correlates well with the fate of internalization of natural oligonucleotides (Akhtar et al., *Nucleic Acids Res.,* 1991, 19, 5551).

Increased cellular uptake of antisense oligonucleotides by adsorptive endocytosis can be obtained by liposome encapsulation. In one study, researchers showed that a 21-mer complementary to the 3'-tat splice acceptor of the HIV-1 was able to markedly decrease the expression of a p24 protein while encapsulated into a liposome containing diastearoylphosphatidylethanol-amine (Sullivan et al., *Antisense Res. Devel.,* 1992, 2, 187). Many other examples have been reported, including pH-sensitive liposomes (Huang et al., *Methods Enzymol.,* 1987, 149, 88) which are well detailed in several good review articles (Felgner et al., *Adv. Drug Deliv. Rev.,* 1990, 5, 163 and Farhood et al., *N.Y. Acad. Sci.,* 1994, 716, 23). When phosphorothioate oligonucleotides, that are complementary to the methionine initiation codon of human intracellular adhesion molecule-1, were encapsulated, a 1000-fold increase of antisense potency was seen relative to the non-encapsulated phosphorothioate oligonucleotide (Bennett et al., *Mol. Pharmacol.,* 1992, 41, 1023). The oligonucleotide delivery systems are good for in vitro cell systems, but have not been shown to be widely applicable to in vivo studies, due to rapid liposome destabilization and non-specific uptake by liver and spleen cells.

Other, non-specific oligonucleotide uptake enhancements attend attaching hydrophobic cholesterol (Letsinger et al., *Proc. Natl. Acad. Sci.,* 1989, 86, 6553) type or phospholipid type molecules (Shea et al., *Nucleic Acids Res.,* 1990, 18, 3777) to the oligonucleotides. It has been shown that the coupling of a single cholesterol moiety to an antisense oligonucleotide increases cellular uptake by 15-fold (Boutorin et al., *FEBS Lett.,* 1989, 254, 129). When the cationic polymeric drug carrier poly(L-lysine) is conjugated to oligonucleotide sequences, a marked increase of non-specific oligonucleotide cellular uptake occurs (Lemaitre et al., *Proc. Natl. Acad. Sci.,* 1987, 84, 648; Leonetti et al., *Gene* 1988, 72, 323; Stevenson et al., *J. Gen. Virol.,* 1989, 70, 2673). This cationic polymer has been used to deliver several types of drugs with cellular uptake mediated by an endocytic-type mechanism. However, the high molecular weight polylysine is cytotoxic even at low concentrations.

Cell surface receptors are good candidates to serve as selective drug targets. The presence of specific receptors implies that natural endogenous ligands are also present. It is the complexation of the ligand with the appropriate receptor that elicits a cascade of cellular events leading to a desired function. An oligonucleotide drug linked to such an endogenous ligand or a synthetic ligand of equal affinity towards the receptor in question, is considered "targeted" to the receptor.

The potential of carbohydrate drug targeting has become increasingly apparent (Shen et al., *N.Y. Acad. Sci.,* 1987, 507, 272; Monsigny et al., *N.Y. Acad. Sci.,* 1988, 551, 399; Karlsson et al., *TIPS* 1991, 12, 265) as an alternate method for site-specific drug delivery. Complex carbohydrates are involved in many cellular recognition processes such as adhesion between cells, adhesion of cells to the extracellular matrix, and specific recognition of cells (Ovarian egg with sperm) by one another (Yamada, K. M., *Annu., Rev. Biochem.,* 1983, 52, 761; Edelman, G. M., *Annu. Rev. Biochem.,* 1985, 54, 135; Hook et al., *Annu. Rev. Biochem.,* 1984, 53, 847; Florman, H. M., *Cell,* 1985, 41, 313. It is also known that the concentrations of various glycosylated proteins that circulate in the blood are constantly regulated by cells in various tissues. Nature controls and regulates such diverse functions with the aid of specific proteins appearing at the surface of various cells, which have the ability to decode the information found in complex carbohydrate structures. These proteins are collectively called lectins and act as receptors for carbohydrates (Goldstein et al., *Nature,* 1980, 285, 66). Many endogenous lectins are expressed at the surface of normal and malignant cells and are involved in many poorly understood biological processes.

The structural information obtained from a large number of mammalian lectins has led to their classification into several families.

TABLE 2

PROPERTIES OF C-TYPE AND S-TYPE ANIMAL LECTINS

| PROPERTY | C-TYPE LECTINS | S-TYPE LECTINS |
|---|---|---|
| $Ca^{++}$-dependance | Yes | No |
| Solubility | Variable | Buffer soluble |
| Location | Extracellular | Intracellular/extracellular |
| State of cysteines | Disulfides | Free thiols |
| Carbohydrate specificity | Different types | Mostly β-galactosides |

The C-lectins or calcium-dependent lectins possess carbohydrate recognition domains (CRDs) of the 115–134 amino acids which contain 18 highly conserved and 14 invariant residues (Drickamer, K., *J. Biol. Chem.,* 1988, 263, 9557; Drickamer, K., *Curr. Opin. Struc. Biol.,* 1993, 3, 393; Drickamer, K., *Biochemical Society Transactions,* 1993, 21, 456). The C-lectins are interesting from a pharmacological point of view since they recognize specific carbohydrates and immediately endocytose the receptor-bound glycoprotein complex via coated pits and vesicles.

These vesicles which are also referred to as endosomes, bring the receptor-glycoprotein complex to other cellular compartments, called the lysozomes, where protein degradation occurs (Breitfeld et al., *Int. Rev. Cytol.,* 1985, 97, 4795). The range of C-type lectin carbohydrate specificity differs form cell to cell and from tissue to tissue.

The first membrane lectin was characterized on hepatocyte liver cells (Van Den Hamer et al., *J. Mol. Biol.,* 1970, 245, 4397). The hepatic asialoglycoprotein receptor (ASGP-R) was isolated by Ashwell and Harford (Ashwell, G.; Herford, J., *Ann. Rev. Biochem.* 1982, 51, 531; Schwartz, A. L., *CRC Crit. Rev. Biochem.,* 1984, 16, 207). These lectins internalized efficiently and cleared plasma levels from ceruloplasmin which contained abnormally truncated N-oligosaccharides lacking the terminal sialic acid residues. Other artificial molecules which have terminal galactose or N-acetylgalactosamine residues have been found to bind with high affinity to this lectin. This unique specificity between the exposed galactose units and the ASGP-R suggested the design and testing of glycotargeting systems and the use of lectins as specific drug delivery targets.

TABLE 3

MEMBRANE SPANNING C-TYPE LECTINS

| NAME | TISSUE | SUGAR SPECIFICITY |
|---|---|---|
| ASGP-R (type II) | Liver Hepatocytes | Galactose and N-acetylgalactoseamine[1] |
| Placental receptor | Placenta | Fucose and mannose[2] (type II) |
| Macrophage receptor | Liver Kupffer cells | Galactose and type II) N-acetyl galactoseamine |
| Kupffer cell receptor | Liver Kupffer cells | Galactose and fucose (type II) |
| IgE Fc receptor | B cells | Galactose[5] (type II) |
| P-selectin | Platelets | Fucose and sialic acid (type IV) |
| E-selectin (type IV) | Endothelial cells | Fucose and sialic (type IV) acid[7] |
| L-selectin | Leukocytes | Fucose and sialic acid[8] (type IV) |
| Mannose receptor | Macrophages | Mannose and fucose[9] (type VI) |

[1]Spiess et al., J. Biol. Chem., 1985, 260, 1979.
[2]Curtis et al., Proc. Natl. Acad. Sci., 1992, 89, 8356.
[3]Ii, et al., J. Biol. Chem., 1990, 265, 11295.
[4]Hoyle et al., J. Biol. Chem., 1988, 263, 7487.
[5]Kikutani et al., Cell, 1986, 47, 657.
[6]Johnston et al., Cell, 1989, 56, 1033.
[7]Bevilacqua et al., Science, 1989, 243, 1160.
[8]Laskyk et al., Cell, 1989, 56, 1045.
[9]Taylor et. al., J. Biol Chem., 1992, 267, 1719.

Many other cell lines, some summarized in Table 2, have surface carbohydrate-type receptors that mediate uptake of various ligands (Drickamer, K., *Cell* 1991, 67, 1029). Immune cells like monocytes and macrophages possess a number of surface glycoproteins that enable them to interact with invading micro-organisms (Gordon et al., *J. Cell Sci. Suppl.*, 1988, 9, 1). Drugs need to be carried to target cells via a carrier or high affinity ligand which is attached to the drug. The different carriers for glycotargeting can be glycoproteins or neoglycoproteins, (glycopeptides or neoglycopeptides) and as glycosylated polymers.

The in vitro glycotargeting principle is relatively simple, but its in vivo applicability is difficult. Synthetic efforts have generated liposomes (also referred as immunoliposomes) and polylysine carriers, in which antibodies and some carbohydrate conjugate ligands have been covalently attached on the outer bilayer. For example, when natural oligonucleotides complementary to the translation initiation region of VSV N protein mRNA were encapsulated with liposomes whose outer membrane had several H2K-specific antibodies to L929 cells, there was a marked decrease in viral replication only within L929 infected cells (Leonetti et al., *Proc. Natl. Acad. Sci.*, 1990, 87, 2448). Receptor-mediated endocytic mechanisms have been exploited by attachment of cell-specific ligands and antibodies to polylysine polymers. For example, c-myb antisense oligonucleotides conjugated with polylysine-folic acid (Citro et al., *Br. J. Cancer* 1992, 69, 463) or polylysine-transferrin (Citro et al., *Proc. Natl. Acad. Sci.*, 1992, 89, 7031) targets were found to better inhibit HL-60 leukemia cell line proliferation than oligonucleotides without conjugated carriers. Another promising polylysine-asialoorosomucoid carrier was conjugated with phosphorothioate oligonucleotides complementary to the polyadenylation signal of Hepatitis B virus (Wu, G. Y.; Wu, C. H., *J. Biol. Chem.*, 1992, 267, 12436).

Methods have been previously developed that utilize conjugates to enhance transmembrane transport of exogenous molecules. Ligands that have been used include biotin, biotin analogs, other biotin receptor-binding ligands, folic acid, folic acid analogs, and other folate receptor-binding ligands. These materials and methods are disclosed in U.S. Pat. No. 5,108,921, issued Apr. 28, 1992, entitled "Method for Enhanced Transmembrane Transport of Exogenous Molecules", and U.S. Pat. No. 5,416,016, issued May 16, 1995, entitled "Method for Enhancing Transmembrane Transport of Exogenous Molecules", the disclosures of which are herein incorporated by reference.

These immunoliposomes and antibody-polymer targeting exhibited no in vivo activity. With similar drawbacks as their non-specific counterparts, the immunoliposome-drug complexes are mostly immunogenic and are phagocytosed and eventually destroyed in the lysosome compartments of liver and spleen cells. As for the antibody-polylysine-drug complexes, they have shown substantial in vitro cytotoxic activity (Morgan et al., *J. Cell. Sci.*, 1988, 91, 231). Other carriers are glycoproteins. On such large structures, a few drug molecules can be attached. The glycoprotein-drug complexes can subsequently be desilylated, either chemically or enzymatically, to expose terminal galactose residues.

Glycoproteins and neoglycoproteins are recognized by lectins such as the ASGP-R. Glycoproteins having a high degree of glycosylation heterogeneity are recognized by many other lectins making target specificity difficult (Spellman, N. W., *Anal. Chem.*, 1990, 62, 1714). Neoglycoproteins having a high degree of homogeneity exhibit a higher degree of specificity for lectins especially the ASGP-R. Many experimental procedures which are used to couple sugars to proteins have been reviewed by Michael Brinkley (Brinkley, M., *Bioconjugate Chem.*, 1992, 3, 2). These neoglycoproteins may mimic the geometric organization of the carbohydrate groups as in the native glycoprotein and should have predictable lectin affinities. Successful in vitro delivery of AZT-monophosphate, covalently attached to a human serum albumin containing several mannose residues was achieved in human T4 lymphocytes (Molema et al., *Biochem. Pharmacol.*, 1990, 40, 2603).

Examples of antisense oligonucleotide-neoglycoprotein complexes have been previously reported (Bonfils et al., *Nucleic Acids Res.*, 1992, 20, 4621). The authors mannosylated bovine serum albumin and attached, covalently from the 3'-end, a natural oligonucleotide sequence. The oligonucleotide-neoglycoprotein conjugate was internalized by mouse macrophages in 20-fold excess over the free oligonucleotide. Biotinylated oligonucleotides, were also disclosed which were non-covalently associated with mannosylated streptavidin (Bonfils et al., *Bioconjugate Chem.*, 1992, 3, 277). Such complexes were also better internalized by macrophages. Other successful examples consisted of antisense oligonucleotides which were non-covalently associated with asialoglycoprotein-polylysine conjugates. Such oligonucleotide conjugates were found to internalize more efficiently into hepatocytes (Bunnel et al., *Somatic Cell Molecular Genetics*, 1992, 18, 559; Reinis et al., *J. Virol. Meth.*, 1993, 42, 99) and into hepatitis B infected HepG2 cells (Wu, G. Y.; Wu, C. H., *J. Biol. Chem.*, 1992, 267, 12436).

Polymeric materials have been assessed as drug carriers and three of them, dextrans, polyethyleneglycol (PEG) and N-(2-hydroxypropyl)methacrylamide (HMPA) co-polymers, have been successfully applied in vivo (Duncan, R., *Anticancer Drugs*, 1992, 3, 175). This research has been focused mainly at treatments for cancer and as a requisite the size of the compounds are between 30–50 kDa to avoid renal excretion (Seymour, L. W., *Crit. Rev. Ther. Drug Carrier Syst.*, 1992, 9, 135).

In order to examine the chemistry and related methodologies involving the preparation of glycoprotein-drug and neoglycoprotein-drug glycoconjugates, certain groups have investigated the use of simpler high affinity ligands for specific drug delivery. Initially, several sugars were attached to small peptides in an attempt to obtain mimics of multivalent N-linked oligosaccharides (Lee, R. T., Lee, Y. C., *Glycoconjugate J.*, 1987, 4, 317; Plank et al., *Biconjugate Chem.*, 1992, 3, 533; Haensler et al., *Bioconjugate Chem.*, 1993, 4, 85).

Other groups investigated the use of sugar clusters lacking a protein backbone and eventually used low molecular weight N-linked oligosaccharides with a minimum carbohydrate population to bind with high affinity to lectins as the ASGP-R. Branched N-linked oligosaccharide-drug conjugates can be used instead of neoglycoprotein-drug complexes. The total synthesis of branched N-linked oligosaccharides is still a difficult task, however they could be obtained by enzymatic cleavage from protein backbones (Tamura et al., *Anal. Biochem.*, 1994, 216, 335). This method requires expensive purifications and only generates low quantities of chemically defined complex oligosaccharides. The affinity of N-linked oligosaccharide clusters towards many lectins has been demonstrated and has helped researchers to locate different new mammalian lectins in animals (Chiu et al., *J. Biol. Chem.*, 1994, 269, 16195).

One process of increasing the intracellular oligonucleotide concentration is via receptor-mediated endocytic mechanisms. This novel drug targeting concept has been demonstrated in vitro by several groups. Oligonucleotides have been attached to glycoproteins, neoglycoproteins and neoglycopolymers possessing a defined carbohydrate population which, in turn, are specifically recognized and internalized by membrane lectins. To the best of our knowledge in vivo applicability of oligonucleotide-carbohydrate conjugates has not been previously demonstrated.

It has also been shown in in vitro experiments that synthetic neoglycoproteins containing galactopyranosyl residues at non-reducing terminal positions are recognized by the ASGP-R with increasing affinity as the number of sugar residues per molecule is increased (Kawaguchi et al., *J. Biol. Chem.* 1981, 256, 2230).

OBJECTS OF THE INVENTION

As in apparent, there exists a need for an improved method of selective delivery of biologically active compounds such as antisense oligonucleotides to specific cells. This invention is directed to providing methods to effect such delivery.

SUMMARY OF THE INVENTION

The present invention provides complexes and methods for using such complexes. The complex forms are useful for enhancing the intracellular uptake of biologically active compounds (primary compounds). The complex compounds of the invention are prepared having the component parts shown below:

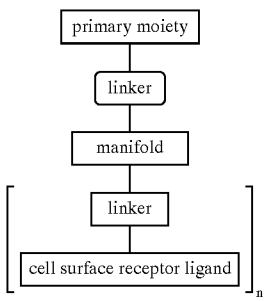

wherein the primary moiety is a nucleotide, nucleoside, oligonucleotide or oligonucleoside; each of said linkers are, independently, bi- or trifunctional; said manifold is derivatized at a plurality of sites; each of said cell surface receptor ligands is a carbohydrate; and n is an integer from 2 to about 8.

Preferably, at least two cell surface receptors are individually linked by linker groups to a manifold compound which is further linked to a primary compound. The cell surface receptor ligands impart affinity to the complexes for cells having surface receptors that recognize the selected cell surface receptor ligands. This interaction is believed to trigger endocytosis of the complex, resulting in an increased uptake by the cell of the primary compound.

In one embodiment of the invention primary compounds are selected to be oligonucleotides or oligonucleosides. Attachment of oligonucleotides or oligonucleosides to a manifold compound, can be conveniently made at the 5' or 3' phosphate of the 5' or 3' terminal nucleotide or nucleoside of the oligonucleotide or oligonucleoside. Alternatively, the phosphate group can be introduced as part of the linker group attached to the manifold moiety. Such a coupling is made by selecting the terminus of the linker to be a hydroxyl group and converting it to a phosphoramidite. The phosphoramidite can then be reacted with an unblocked 2', 3' or 5' hydroxyl group of an oligonucleotide or oligonucleoside.

Manifold species as used in the present invention can include a wide variety of compounds that have functional groups or sites that can be linked by linker groups to a primary compound together with a cell surface receptor ligand, or, preferably ligands. In one embodiment a polycyclic molecule may be selected as the manifold compound, as can be illustrated for cholic acid. In other embodiments a smaller, monocyclic manifold compound can be selected, such as phenyl or cyclohexyl.

Manifold compounds can also comprise branched chain aliphatic compounds that have the funtionalities available for linking. Also, combinatorial chemistry techniques are known to utilize numerous compounds that can be used as manifold compounds. Many combinatorial scaffolds are ammenable for use as manifold compounds by virtue of their multiple reactive sites, which can be subjected to various orthogonal protection schemes. Preferable reactive sites include hydroxyl groups, carboxylic acid groups, amino groups and thiol groups.

Linker groups that are preferred for use in the present invention can be selected for a variety of chemical reasons. If the primary compound is an oligonucleotide or oligonucleoside, a linker can be conveniently chosen having a secondary hydroxyl group and/or a primary hydroxyl group with an additional functionality such as an amino, hydroxyl, carboxylic acid, or thiol group. The additional functionality can be used to attach one end of the linker group to the manifold moiety by for example an amide linkage. The secondary and or primary hydroxyl groups can be used to prepare a DMT or DMT phosphoramidite as illustrated in the Example section. This enables the attachment to an oligonucleotide or oligonucleoside to a solid support or to the 2', 3' or 5' position or a ribosyl group. This will allow variability of the placement of the conjugated manifold compound to the primary compound. In a preferred embodiment an oligonucleotide is prepared using standard automated solid support protocols as is well known in the art and the conjugated manifold compound is coupled as the last step to the 5'-O position of the completed oligonucleotide or oligonucleoside. Cleavage from the solid support will give the complex compound.

For use in antisense and similar methodologies, oligonucleotides and oligonucleosides of the invention preferably comprise from about 10 to about 30 subunits. It is more preferred that such oligonucleosides comprise from about 15 to about 25 subunits. As will be appreciated, a subunit is a base and sugar combination suitably bound to adjacent subunits through, for example, a phosphorous-containing (e.g., phosphodiester) linkage or some other linking moiety. The nucleosides need not be linked in any particular manner, so long as they are covalently bound. Exemplary linkages are those between the 3'- and 5'-positions or 2'- and 5'-positions of adjacent nucleosides. Exemplary linking moieties are disclosed in the following references: Beaucage, et al., *Tetrahedron* 1992, 48, 2223 and references cited therein; and U.S. patent applications: Ser. No. 703,619, filed May 21, 1991; Ser. No. 903,160, filed Jun. 24, 1992; Ser. No. 039,979, filed Mar. 20, 1993; Ser. No. 039,846, filed Mar. 30, 1993; and Ser. No. 040,933, filed Mar. 31, 1993. Each of the foregoing patent applications are assigned to the assignee of this invention. The disclosure of each is incorporated herein by reference.

In other embodiments of the invention, primary compounds comprise oligonucleotides or oligonucleosides attached through a linking moiety to the manifold moiety such as by a free 2'-, 3'-, or 5'-hydroxyl group. Such attachments are prepared by, for example, reacting nucleosides bearing at least one free 2'-, 3'-, or 5'-hydroxyl group under basic conditions with a linking moiety having a leaving group such as a terminal L—(CH$_2$)-etc. function, where L is a leaving group. Displacement of the leaving group through nucleophilic attack of (here) an oxygen anion produces the desired derivative. Leaving groups according to the invention include but are not limited to halogen, alkylsulfonyl, substituted alkylsulfonyl, arylsulfonyl, substituted arylsulfonyl, hetercyclcosulfonyl or trichloroacetimidate. A more preferred group includes chloro, fluoro, bromo, iodo, p-(2,4-dinitroanilino)benzenesulfonyl, benzenesulfonyl, methylsulfonyl(mesylate), p-methylbenzenesulfonyl(tosylate), p-bromobenzenesulfonyl, trifluoromethylsulfonyl(triflate), trichloroacetimidate, acyloxy, 2,2,2-trifluoroethanesulfonyl, imidazolesulfonyl, and 2,4,6-trichlorophenyl, with bromo being preferred.

Suitably protected nucleosides can be assembled into an oligonucleosides according to many known techniques. See, e.g., Beaucage, et al., *Tetrahedron* 1992, 48, 2223.

A wide variety of linker groups are known in the art that will be useful in the attachment of primary compounds to manifold compounds. Many of these are also useful for the attachment of cell surface receptor ligands to the manifold compound. A review of many of the useful linker groups can be found in *Antisense Research and Applications*, S. T. Crooke and B. Lebleu, Eds., CRC Press, Boca Raton, Fla., 1993, p. 303–350. A disulfide linkage has been used to link the 3' terminus of an oligonucleotide to a peptide (Corey, et al., *Science* 1987, 238, 1401; Zuckermann, et al., *J. Am. Chem. Soc.* 1988, 110, 1614; and Corey, et al., *J. Am. Chem. Soc.* 1989, 111, 8524). Nelson, et al., *Nuc. Acids Res.* 1989, 17, 7187 describe a linking reagent for attaching biotin to the 3'-terminus of an oligonucleotide. This reagent, N-Fmoc-O-DMT-3-amino-1,2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy, et al., *Tetrahedron Letters* 1991, 32, 879. A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg, et al., *Antisense Research and Development* 1991, 1, 161 to link fluorescein to the 5'-terminus of an oligonucleotide. Other compounds such as acridine have been attached to the 3'-terminal phosphate group of an oligonucleotide via a polymethylene linkage (Asseline, et al., *Proc. Natl. Acad. Sci. USA* 1984, 81, 3297).

Oligonucleotides have been prepared on solid support and then linked to a peptide via the 3' hydroxyl group of the 3' terminal nucleotide (Haralambidis, et al., *Tetrahedron Letters* 1987, 28, 5199). An Aminolink 2 (Applied Biosystems, Foster City, Calif.) has also been attached to the 5' terminal phosphate of an oligonucleotide (Chollet, *Nucleosides & Nucleotides* 1990, 9, 957). This group also used the bifunctional linking group SMPB (Pierce Chemical Co., Rockford, Ill.) to link an interleukin protein to an oligonucleotide.

In another embodiment of the invention, linker moieties are used to attach manifold groups to the 5 position of a pyrimidine (Dreyer, et al., *Proc. Natl. Acad. Sci. USA* 1985, 82, 968). Fluorescein has been linked to an oligonucleotide in the this manner (Haralambidis, et al., *Nucleic Acid Research* 1987, 15, 4857) and biotin (PCT application PCT/US/02198). Fluorescein, biotin and pyrene were also linked in the same manner as reported by Telser, et al., *J. Am. Chem. Soc.* 1989, 111, 6966. A commercial reagent, Amino-Modifier-dT, from Glen Research Corporation (Sterling, Va.) can be utilized to introduce pyrimidine nucleotides bearing similar linking groups into oligonucleotides.

Cholic acid linked to EDTA for use in radioscintigraphic imaging studies was reported by Betebenner, et. al., *Bioconjugate Chem.* 1991, 2, 117.

In a preferred embodiment of the present invention, novel complex compounds are prepared having oligonucleotide conjugates that are useful for oligonucleotide antisense drug targeting of, for example, the carbohydrate recognition domains (CRD) found on the asiologlycoprotein-receptor (ASGP-R). These complex compounds were prepared according to the principles which govern the specificity of the {ligand-[ASGP-R]} complex. Simple carbohydrates and Glycoconjugates having only one linked saccharide moiety show a slight affinity for the receptor (Lee et al., *Biol. Chem.*, 1983, 258, 199). For instance, glycoconjugates having monovalent ligands such as galactose, lactose or monoantennary galactosides (one carbohydrate group attached via a linkage to the scaffold) bind to this ASGP-R with a millimolar dissociation constant. When binary oligo-saccharides (two carbohydrate groups each attached via a linkage to the scaffold) are used, the dissociation constants are in the micromolar range. This translates to a three order of magnitude higher affinity. When trinary oligosaccharides (three carbohydrate groups each attached via a linkage to the scaffold) are tested, the dissociation constants are in the nanomolar range.

Based on dissociation constants, e.g. higher for 3 carbohydrate groups, trinary oligosaccharides were preferably synthesized, each having three carbohydrate groups independently linked to a scaffold which was further linked to an oligonucleotide. The resulting low molecular weight oligonucleotide conjugates were easily amenable to automated DNA synthesis methodology. The oligonucleotide conjugates each consist of at least four distinct moieties, scaffold, carbohydrate attaching linker, oligonucleotide attaching linker, and carbohydrate.

Initially, cholic-acid was chosen as a scaffold. Cholic acid was chosen because it is a natural product in mammalian systems, does not form a toxic metabolite and because it is commercially available at low cost. Another reason for choosing cholic acid was that this steroidal scaffold would be a good anchor for linked carbohydrates, separating the points of attachment and reducing any steric interference between them. Increasing the distance between points of attachment of the linked carbohydrates would increase the degree of freedom and reduce the length requirement of the linker to obtain high affinity with the receptor.

Galactose and lactose were initially chosen as carbohydrate moieties since they are recognized by the carbohydrate recognition domains (CRD) found on the asiologlycoprotein-receptor (ASGP-R).

Aminocaproate, derived from commercially available N-Fmoc-ε-aminocaproic acid, was chosen as the carbohydrate linker and its length was based on previously reported experimental evidence (Biessen et al., *J. Med. Chem.*, 1995, 38, 1538). The previously reported results indicated that cluster galactosides between 10 and 20 Å in length were high affinity substrates for the hepatic ASGRP-R. The length of the linking group was initially chosen to be eight atoms long because in conjunction with the larger area scaffold being used the result may be better positioning of the carbohydrate components towards the CRD's of ASGP-R.

After the cholic acid scaffold has been linked to each of the carbohydrates and a linker group is deblocked and ready for attachment an oligonucleotide is coupled. The preferred method of coupling of the conjugate to an oligonucleotide is to perform the coupling while the full length oligonucleotide is bound to solid support. The conjugate is coupled to the oligonucleotide followed by cleavage of the final product from the solid support. This cleavage step also removes acetyl protecting groups present on any hydroxyl groups that were previously protected especially on any saccharide moieties.

The oligonucleotide analog is tested for affinity towards the ASGP-R expressed on several cells. The binding of the oligonucleotide conjugate to the ASGP-R should initiate the internalization process and increase the intracellular concentration of the selected oligonucleotide.

It will be appreciated that modified nucleotide moieties may also be useful in connection with embodiments of this invention. Thus, a wide variety of chemical modifications may be employed throughout the nucleic acids. Thus modifications of pyrimidine or purine bases, substitutions at the 2' position, alteration of inter-nucleoside linkages, carbohydrate ring substitutions and positional variations may all be employed.

Teachings regarding the synthesis of modified oligonucleotides may be found in the following U.S. patents or pending patent applications, each of which is commonly assigned with this application: U.S. Pat. Nos. 5,138,045 and 5,218, 105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, issued Jun. 29, 1993, and 5,608,046, both drawn to conjugated 4'-desmethyl nucleoside analogs; U.S. Pat. Nos. 5,602,240, and 5,610, 289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

It is to be understood that all modifications to nucleotides, nucleosides at oligonomers thereof are encompassed within their respective definitions.

Antisense oligonucleotides are conversely synthesized using automated DNA synthetic methodology.

Therefore, small glycotargeting systems, which can be incorporated into the last cycle of an automated DNA synthesis, are preferred.

EXAMPLE 1

Synthesis of 2,3,4,5-aceto-1-bromo-α-D-galactose

The title compound was synthesized using slightly modified, known procedures to generate the acetobromogalactose (Methods in Carbohydrate Chemistry, Wistler and Wollfrom, Eds, Academic Press; New York, 1962; Vol. 1–6). Dry D-galactose was reacted with acetic anhydride (20 eq.) in the presence of a catalytic amount of DMAP (0.1 eq.) in dry pyridine at 0° C. After 1 hour at 0° C., the reaction mixture was allowed to warm to room temperature. After 6 hours had passed the thick solution was poured into a rapidly stirred solution of ice-water (500 mL). A sticky precipitate developed and was extracted with ethyl acetate. 1,2,3,4,5-pentaacetyl-α-D-galactose was obtained as a slightly yellow oil in 89% yield.

The 1,2,3,4,5-pentaacetyl-α-D-galactose was used without further purification in the next step by treatment with HBr (5 molar eq., 30% solution in glacial acetic acid). After one hour, the HBr and the acetic acid was removed, giving rise to the title a-bromogalactoside as a thick brown oil in 94% yield which was used for the next step without further purification.

EXAMPLE 2

Synthesis of α-D-lactosyl Acid Bromide

Following the procedures illustrated for Example 1 above, dry D-lactose was transformed to octaacetylated D-lactose, which was obtained as a 20:80 mixture of α/β-anomers (α-anomer: doublet, 6.19 ppm, $J_{H1'-H2'}$=3.7 Hz, H1'; β-anomer: doublet, 5.1 ppm, $J_{H1'-H2'}$=8.4 Hz, H1') in 76% yield. The octaacetate was used without further purification by treatment with a solution of HBr (5 molar eq., 30% solution in glacial acetic acid). After the lactosyl compound dissolved (~4–5 min.), the HBr and the acetic acid were quickly removed to avoid hydrolysis of the β(1–4)-O-glycosidic linkage. The title compound was obtained as a thick brown oil in 97% yield. The title compound was used without further purification in the next step.

EXAMPLE 3

Synthesis of Peracetylated-β-azidogalactose 2,3,4,5-Aceto-1-bromo-α-D-galactose was reacted under phase transfer catalysis (PTC) conditions previously reported (Tropper et al., *Ph.D Thesis, University of Ottawa*, 1992.) with 5 eq. of sodium azide in the presence of tetrabutylammonium hydrogen sulfate (PTS) (1 eq.) in a 1:1 mixture of $CH_2Cl_2$ and $NaHCO_3$ (saturated solution). After 3 hours, under vigorous stirring, the title compound was obtained as a pale yellow solid in 97% yield. The characteristic $^1$H-NMR [anomeric α-H; 4.56 ppm ($^3J_{H1'-H2'}$=8.6 Hz)] and $^{13}$C-NMR [anomeric C-1'; 88.29 ppm] data confirmed the structure and was in agreement with published data. This reaction occurred with complete inversion ($^3J_{H1'-H2'}$=8.6 Hz confirmed the 1,2-trans-β-D-anomeric configuration) and therefore established the desired stereochemistry.

EXAMPLE 4 peracetylated-β-azidolactose

Following the procedures illustrated for Example 1 above, α-D-lactosyl acid bromide was converted to the β-azidolactose. The title compound was obtained as a pale orange oil in 92% yield. The characteristic $^1$H-NMR [glucose anomeric α-H; 4.6 ppm ($^3J_{H1'-H2'}$=8.8 Hz)] and $^{13}$C-NMR [glucose anomeric C-1'; 88.30 ppm] data confirmed the structure and was in agreement with published data (Tropper et al., *Synthesis*, 1992, 7, 618). The PTC reaction occurred with complete inversion as observed for the peracetylated-β-azidogalactose.

EXAMPLE 5

Synthesis of Peracetylated-β-aminogalactose

Hydrogenation of peracetylated-β-azidogalactose in the presence of a large excess of Pd (10% on charcoal in wet methanol) at 40 p.s.i. for 1 hour gave peracetylated-β-aminogalactoside as a pale yellow oil in quantitative yield. The characteristic $^1$H-NMR data (the clean doublet of the anomeric proton in the azide shifted from 4.6 ppm to a multiplet at 5.37–5.39 ppm in amine, indicating the absence of the anomeric azide group) and the mass spectrum analysis (CI-NH3: m/e 347 [M]$^+$) confirmed the structure.

EXAMPLE 6

Synthesis of Peracetylated-β-aminolactose

As per the procedures illustrated in Example 5, peracetylated-β-azidolactose was hydrogenated under similar reaction conditions. The β-azide was hydrogenated in the presence of Pd (10% on charcoal in wet methanol). After a simple celite filtration, the title compound was obtained in quantitative yield as a pale yellow oil. The characteristic $^{13}$C-NMR data (the galactose anomeric carbon was at 101.14 ppm and the glucose anomeric carbon shifted from 87.71 ppm in azide 4a to 84.48 ppm) and the mass spectrum analysis (FAB-NBA: m/e 636 [M+H]$^+$) confirmed the structure.

The reduction reactions of Example 5 and 6 were adapted from Tropper ibid. In this previously reported procedure stoichiometric amounts of catalyst to glycosyl azides was used. This procedure was found to be quite dangerous when synthesizing on large scales so the amount of Pd was reduced to 0.2 to 0.4 eq. of Pd on carbon (10%). This amount was sufficient to reduce the glycosyl azides without affecting the acetates (no deacetylated galactosamines or lactosamines were detected by $^1$H-NMR or $^{13}$C-NMR on the crude mixtures).

Due to the instability of both glycosylamines, no purification was performed prior to coupling with the linkers.

EXAMPLE 7

Attachment of N-Fmoc (9-fluorenylmethoxycarbonyl) Protected ε-aminocaproic Acid Linker to Peracetylated-β-aminogalactose N-Fmoc-ε-aminocaproic acid (Scheme 8) is treated with O-benzotriazol-1-yl-N,N,N',N'-tetramethyluronium hexafluorophosphate (HBTU, 1 eq.) in the presence of 1-hydroxybenzotriazole (HOBt) (1 eq.) and N-methylmorpholine (NMM) (1.5 eq.) in dry DMF. After 35 min. at r.t., peracetylated-β-aminogalactose was added and the reaction was stirred for an additional 18 hours. The reaction mixture is concentrated and purified by chromatography to give the galactosylamide in a 45% yield. In this reaction, the anionic form of the acid attacks the HBTU forming the acyloxyphosphonium salt. This reactive salt is attacked by either ionized HOBt or ionized acid, forming the benzotriazolyl active ester and symmetrical anhydride, respectively. The glycosylamine reacts with either of the reactive intermediates to yield the desired product.

The amide NH appeared as sharp doublet at 6.24 ppm (in CDCl$_3$) and coupled strongly (from 2D-COSY) to the anomeric multiplet at 5.18–5.27 ppm (3JNH-H1'=9.15 Hz). From $^{13}$C-NMR spectrum, the C-1' anomeric carbon was at 78.5 ppm. All the NMR data and the mass spectrum (FAB-NBA: m/e 683 [M+H]$^+$) confirmed the desired structure.

Other attempts to increase the coupling efficiency were investigated by using the BOP reagent instead of HBTU. N-Fmoc-ε-aminocaproic acid was reacted with BOP (1 eq.) reagent in the presence of HOBt (1 eq.) and NMM (1.5 eq.) in dry DMF. After 1 hour at r.t., the galactosylamine was added and 18 hours later the galactosylamide was obtained in a 51% yield after column chromatography.

The BOP method gave comparable yields and was the preferred reagent being approximately three times cheaper than HBTU. Triethylamine (TEA) was used instead of NMM since the latter is used in peptide coupling methodology as a racemization suppressant. In the synthesis, there is no racemization and the use of triethylamine gave comparable results.

EXAMPLE 8

Attachment of N-Fmoc Protected Linker to Peracetylated-β-aminolactose

The attachment of an N-Fmoc protected linker to peracetylated-β-aminolactose is accomplished following the procedure of Example 7. N-Fmoc-ε-aminocaproic acid was treated with BOP reagent (1 eq.) in the presence of HOBt (1 eq.) and triethylamine (1.5 eq.) in dry DMF. After 1 hour at r.t., peracetylated-β-aminogalactose was added and the reaction was stirred for an additional 24 hours. Following a previously reported procedure (Coste et al., *J. Org. Chem.*, 1994, 59, 2437) a 10% citric acid solution was used instead of a saturated solution of NH₄Cl to efficiently extract the BOP and other by-products from the organic layer of the BOP coupling reaction. The stronger acidic solution extracted most of the BOP and the trace amounts of the active ester and the symmetric anhydride intermediates, which greatly simplified the chromatographic purification. The lactosylamide product was obtained after column chromatography in 51% yield. From the $^1$H-NMR spectrum, the amide NH at 6.64 ppm appeared as a doublet ($^3J_{NH-H1'}$=9.3 Hz) The glucose H1' overlapped with the H3' glucose and a multiplet was observed between 5.11 and 5.21 ppm. The glucose H2' was a clean apparent triplet (J=9.8 Hz) which confirmed the β-amide linkage through the 1,2-trans arrangement between H2'–H1' and between H2'–H3'. The galactose and glucose anomeric carbons were at 100.8 and 77.8 ppm, respectively. From FAB-MS, the pseudomolecular ion at 971 ([M+H]⁺) and some characteristic fragments (749 [M+H—Fmoc]⁺ and 619 [M+H—{Fmoc-NH—CH₂(CH₂)₄—C(O)NH}]⁺) were in agreement with the assigned structure.

EXAMPLE 9

Fmoc Cleavage of Peracylated-β-N-[ε-(N-Fmoc) aminocaproic]aminogalactose with Piperidine and TBAF

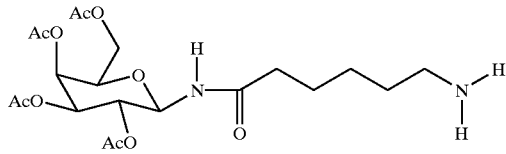

The peracylated-β-N-[ε-(N-Fmoc)aminocaproic] aminogalactose (product from Example 7) was treated with tetrabutylammonium fluoride (TBAF) (1.2 eq., from a 0.1 M stock solution) (see Ueki et al., *Tetrahedron Lett.*, 1997, 26, 560). After 2 hours at room temperature, the reaction mixture was diluted with ethyl acetate and thoroughly washed with water. After chromatographic purification, peracylated-β-N-(ε-aminocaproic)aminogalactose was obtained in 29% yield. Characteristic $^1$H-NMR data (sharp singlet at 2.11 ppm corresponding to the free amine NH due to fast exchange from hydrogen bonding and loss of all Fmoc proton signals) and mass spectrometry (FAB-NBA m/e: 461 [M+H]⁺, 100% relative intensity) confirmed the assigned structure.

EXAMPLE 10

Fmoc Cleavage of Peracylated-β-N-[ε-(N-Fmoc) aminocaproic]aminolactose with Piperidine and TBAF

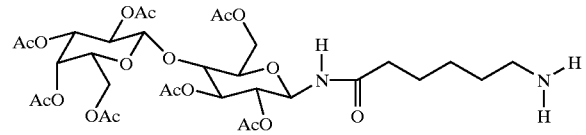

The peracylated-β-N-[(ε-(N-Fmoc)aminocaproic] aminolactose (Example 8) was treated with TBAF (1.2 eq.) in dry DMF for 3 hours at room temperature. The free amine product was obtained after chromatography in a 55% yield. Characteristic $^1$H-NMR data [a sharp singlet at 2.12 ppm, overlapping with the α-methylene protons to the amide linkage (lac-NHC(O)CH₂—), corresponded to the free amine NHD and the loss of all Fmoc proton signals] and mass spectrometry (FAB-NBA m/e: 749 [M+H]⁺) confirmed the assigned structure.

EXAMPLE 11

Coupling of Glycosylamines with the N-carbobenzyloxy (Cbz) Protected Linkers

Commercially available N-Cbz-ε-aminocaproic acid was treated with BOP reagent (1 eq.) in the presence of HOBt (1 eq.) and triethylamine (1.6 eq.) in dry DMF for 30 minutes. Peracetylated-β-aminogalactose (Example 5) was added and stirring was maintained for an additional 48 hours. The organic layer was washed with a 10% citric acid solution to remove most of the BOP and trace amounts of reactive intermediates. The coupled galactosylamine having the Cbz protecting group on the ε-amino end of the amino caproic acid linker was obtained after chromatography in a 60% yield. From $^1$H-NMR spectrum the amide NH appeared as a sharp doublet at 6.43 ppm ($^3J_{NH-H1'}$=9.3 Hz). The anomeric proton appeared as a doublet of doublets at 5.20 ppm ($^3J_{H1'-NH}$=9.3 Hz, $^3J_{H1'-H2'}$=8.7 Hz) which confirmed the 1,2-trans arrangement of H1'–H2' and the β N-glycosidic bond. The anomeric carbon was at 78.4 ppm in the $^{13}$C-NMR spectrum and the mass spectra [Electrospray MS m/z: 617.4 [M+Na]⁺, 100; and high resolution (FAB-NBA) m/e: 595 [M+H]⁺, calc. for C₂₈H₃₉N₂O₁₂, 595.2424; found 595.2503] confirmed the assigned structure.

EXAMPLE 12

Coupling of Peracetylated-β-aminolactose with N-Cbz-ε-aminocaproic Acid

The ε-amino Cbz protected linked peracylated-β-aminolactose was prepared following the procedures illustrated in Example 11. The product was obtained in a 63% yield after column chromatography. From the $^1$H-NMR spectrum the amide NH appeared as a sharp doublet at 6.14 ppm ($^3J_{NH-H1'(Glu)}$=9.3 Hz) and the anomeric glucose proton appeared at 5.18 ppm as a doublet of doublets $^3J_{H1'-H2'}$=9.5 Hz, $^3J_{H1'-NH}$=9.3 Hz) which confirmed the β-N-linkage. The galactose H1 appeared as a broad doublet at 4.43 ppm ($^3J_{H1'(gal)-H2'}$=7.8 Hz). Mass spectrometry [Electrospray MS m/z: 905.5 [M+Na]⁺, 85.2 and 883.5 [M+H]⁺, 100; FAB-NBA m/e: 595 [M+H]³⁰ , calc. for C₄₀H₅₅N₂O₂₀, 883.3191; found 883.3348] confirmed the assigned structure.

EXAMPLE 13

Cleavage of the Cbz of Peracylated-β-N-[ε-(N-Cbz) aminocaproic]aminogalactose

Peracylated-β-N-[ε-(N-Cbz)aminocaproic] aminogalactose was dissolved in ethyl acetate/water/acetic acid solvent together with an equivalent weight of palladium (10% on activated charcoal as catalyst). The mixture was agitated for 1 hour at a pressure of 40 p.s.i. hydrogen. The $^1$H-NMR spectrum was very clean with a characteristic sharp singlet at 2.31 ppm corresponding to the free amine. All the starting material was consumed and no Cbz proton signals were observed.

EXAMPLE 14

Cleavage of the Cbz of Peracylated-β-N-[ε-(N-Cbz) aminocaproic]aminolactose Hydrogenolysis The cleavage of the Cbz group from peracylated-β-N-[ε-(N-Cbz) aminocaproic]aminolactose was performed following the procedures of Example 13. The $^1$H-NMR spectrum was very clean as observed in the galactosyl series of Example 13.

EXAMPLE 15

Synthesis of Tetrahydroxycholane, Cholane-type Anchoring Backbone

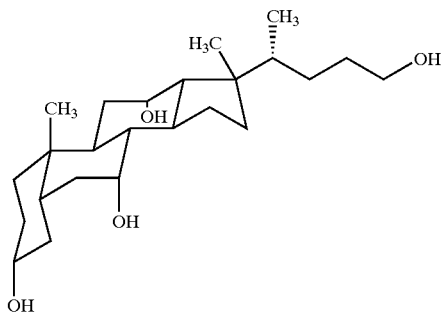

Cholic acid was reacted with borane (4 eq.) THF complex (BH$_3$.THF) in THF at 0° C. Recrystallization of the crude material from isopropanol gave the tetrahydroxycholane in a 75% yield. The m.p. was found to be 224–225° C. The methylene protons at position 24 (—CH$_2$OH) appeared as a broad triplet at 3.50 ppm in the $^1$H-NMR spectrum. The carboxylate carbon of cholic acid, usually found at ~170 ppm, was absent in the $^{13}$C-NMR spectrum of the product. The NMR data and the mass spectrum (FAB-glycerol m/e 789 [2M+H]$^+$ and 395 [M+H]$^+$) confirmed the expected structure.

EXAMPLE 16

Synthesis of the t-butyldiphenylsilyl (TBDPS) Ether of Tetrahydroxycholane

Tetrahydroxycholane (Example 15) was reacted with TBDPSCl (1 eq.) in the presence of imidazole (2 eq.) in dry DMF at 0° C. After purification by chromatography the TBDPS product was obtained in an 89% yield. From the $^1$H-NMR spectrum in CDCl$_3$, the methylene protons at position 24 (—CH$_2$OSi—) appeared as a sharp triplet at 3.60 ppm (J=6.0 Hz). A sharp singlet at 1.01 ppm corresponded to the tert-butyl group and the phenyl protons appeared between 7.33 and 7.68 ppm. The NMR data and the mass spectrum (FAB-NBA m/e 655 [M+Na]$^+$) confirmed the assigned structure.

EXAMPLE 17

Succinimide Activation of TBDPS Ether of Tetrahydroxycholane, Synthesis of the Active Ester The TBDPS ether of tetrahydroxycholane (Example 16) was reacted with triphosgene (2 eq.) in dry pyridine for 15 minutes with the temperature maintained at 0° C. N-hydroxysuccinimide (NHS) (10 eq.) was added and the mixture became cloudy and thickened. Within 10 minutes of the addition of the NHS the mixture started to become light pink and the color intensified slowly over the next 20–25 minutes to light red. After 30 minutes the reaction mixture was poured into cold water and the active ester precipitated out of the solution. Recrystallization from 95% methanol gave a yield of 76% of the active ester. In the $^1$H-NMR spectrum (Example 19), the 3-,7- and 12-α-CH protons appeared at 4.56–4.62 (m), 4.87–4.88 (m) and 5.04 (s) ppm. The downfield shift of all the α-CH and the multiplet at 2.75–2.83 ppm, corresponding to the 12 succimidyl methylene protons [—(O)C—CH$_2$CH$_2$C(O)—] confirmed the tris activation. The NMR data and the mass spectrum (electrospray MS m/z: 1078.6 [M+Na]$^+$; 1056.5 [M+H]$^+$) confirmed the structure.

EXAMPLES 18–24

Preparation of Tris Peracylated Galactose and Tris Peracylated Lactose Conjugates of Formula

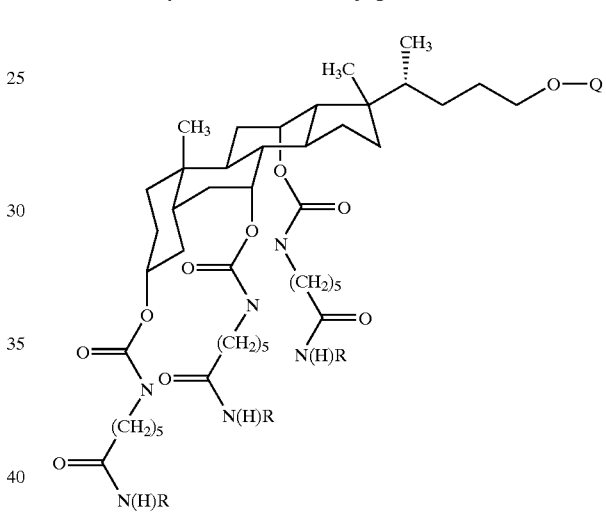

| Example # | R | Q |
|---|---|---|
| 18 | peracylated galactose | TBDPS |
| 19 | peracylated lactose | TBDPS |
| 20 | peracylated galactose | OH |
| 21 | peracylated lactose | OH |
| 22–24 | peracylated lactose | DMT |
| 25 | peracylated lactose | OH |

EXAMPLE 18

Tris Coupling of Peracylated-β-N-(ε-aminocaproic) aminoperacylated Galactose to the NHS Active Ester Active ester (500 mg) was reacted with peracylated-β-N-(ε-aminocaproic)aminoperacylated galactose in dry DMF. After 15 hours at r.t., the reaction mixture was poured into ice cold water and the resulting precipitate was collected and dried under reduced pressure for 24 hours. The 960 mg of product, collected from running the above reaction sequence twice and combining the products, was dissolved in dry pyridine containing acetic anhydride (20 eq.). The mixture was allowed to stir for twelve hours and then was poured into 200 mL of ice water. The resulting pale yellow precipitate was isolated and dried to give a ~90% yield. Further purification was not needed as only one spot was obtained by TLC with an $R_f$=0.4 in 5% MeOH/CH$_2$Cl$_2$. The $^1$H-NMR spectrum was quite complex. The compound was very soluble in CDCl$_3$ and CD$_2$Cl$_2$, but strangely yielded broad and undefined proton resonances. We do not understand the factors involved. One can speculate that such molecules fold, interact and relax differently from non-polar to polar solvents. Only DMSO-d$_6$ could be used to obtain high resolution spectrum. The three anomeric protons appeared at 5.31 ppm as an apparent triplet. Although a J value can be extracted (J=9.3 Hz), it is misleading to use this coupling constant since three triplets are superimposed. At 2.85 to 3.01 ppm, a complex set of multiplets integrated for 6H and corresponded to the 3 [—CH$_2$—NH—C(O)O—] protons. In the acetyl CH$_3$ region between 1.92 and 2.07 ppm, 5 singlets and one multiplet integrated for 36H and correlated well with trisubstitution. Both the NMR data and the electrospray mass spectra {(iPrOH/DMF/TFA) m/z: 2092.4 [M+H]$^+$, 1588.1 [M+H—C$_{21}$H$_{31}$N$_2$O$_{12}$]$^+$, 1083.8 [M+H—C$_{42}$H$_{62}$N$_4$O$_{24}$]$^+$ and 461 [M+H—C$_{83}$H$_{119}$N$_4$O$_{27}$Si]$^+$; (DMF/TFA/AcOH) m/z: 2092.4 [M+H]$^+$; (DMF/CsI) m/z: 2224.2 [M+Cs]$^{2+}$} confirmed the assigned structure.

EXAMPLE 19

Tris Coupling of Peracylated-β-N-(ε-aminocaproic) aminoperacylated Lactose to the NHS Active Ester, Tris-coupled Peracylated Galactose Conjugate The NHS active ester was tris coupled to peracylated-β-N-(ε-aminocaproic)aminoperacylated galactose (Example 14) following the procedures illustrated in Example 18. NHS active ester was reacted with lactosylamine (3.3 eq.) in dry DMF at room temperature. After 18 hours, the reaction mixture was poured into ice water and the trisubstituted lactosyl glycoconjugate was obtained in 87% yield. The mono-deacetylated material (less than 10% by electrospray mass spectra) was reacetylated by treatment with acetic anhydride.

The $^1$H-NMR spectrum of the title compound was complex. Three sets of complex multiplets at 5.10–5.28 ppm integrating for 12H corresponded to three glucose anomeric protons, three H4' (peracylated galactose), three H3' (glucose) and three H3' (peracylated galactose), as deduced from 2D-COSY spectra. The three H1' (glucose) overlapped and appeared as one apparent triplet with $^3$J-coupling values (9.0 and 12.0 Hz) which are not accurate for any of the three anomers. Between 0.68 and 2.08 ppm, a complex area was found to integrate to ~170H. The integration accounted for all the steran H and —CH$_3$ groups, 9 —CH$_2$—caproic groups, 3—CH$_2$—groups adjacent to the amide linkage, and 63H for the 21 acetyl —CH$_3$ groups. From $^{13}$C-NMR, the peracylated galactose anomeric carbon was at 99.78 ppm and the glucose anomeric carbon at 76.54 ppm. The NMR data and the mass spectrum [electrospray (DMF) m/z: 2978.2 [M+Na]$^+$; 2186.2 [M+Na—C$_{33}$H$_{47}$N$_2$O$_{20}$]$^{108\,+}$] confirmed the assigned structure.

EXAMPLE 20

Fluoride-promoted Desilylation of Tris-coupled Peracylated Galactose Conjugate

The peracylated galactose conjugate (title compound of Example 18) was desilylated by treatment with TBAF (25 eq.) in the presence of AcOH (12 eq.) in dry THF. After 1 hour at room temperature additional TBAF (13 eq.) was added and the progress of the reaction was closely monitored. After 30 minutes from the second addition of TBAF, there was still starting material left and a third spot (below the product) appeared. The reaction mixture was immediately poured into ice water to avoid further deacetylation of the product. A sticky precipitate developed and was extracted in ethyl acetate.

Several water washes were performed to remove the excess TBAF and after silica gel column chromatography using 2–2.5% MeOH in CH$_2$Cl$_2$, three fractions were obtained. The first consisted of some starting material which overlapped wish the desilylated product (two spots; top $R_f$=0.28, bottom $R_f$=0.21 in 5% MeOH/CH$_2$Cl$_2$; 19%). The middle fractions consisted essentially of desilylated tris-coupled peracylated galactose conjugate (one middle spot; $R_f$=0.21 in 5% MeOH/CH$_2$Cl$_2$; 55%) and the last fraction was a mixture of desilylated product and deacetylated by-products (~15%). The TBAF method was sufficiently acceptable for the synthesis of 500 mg of pure desilylated tris-coupled peracylated galactose conjugate, required for biological testing.

The $^1$H-NMR in DMSO-d$_6$ (middle spot, 23) was very sharp and several assignments were made (FIG. 22). Three carbamate NH's appeared as broad multiplets between 6.60 and 6.84 ppm. The three H1' protons appeared at 5.32 ppm as a sharp apparent triplet. The H2' protons appeared between 4.97 and 5.02 ppm as a multiplet with triplet-like character.

The 500 MHZ $^1$H-NMR and 2D-COSY spectrum of the desilylated tris-coupled peracylated galactose conjugate showed 24-OH groups appeared between 3.30 and 3.40 ppm as a very intense broad singlet which overlapped with residual water. The t-butyl and phenyl group H's were absent. The above NMR data and the electrospray mass analysis [(DMF/AcOH) m/z: 1876.7 ([M+H+Na]$^+$, 100), 1854.4 ([M+H]$^+$, 5.15), 1371.8 ([M+H-1-C$_{21}$H$_{31}$N$_2$O$_{12}$+Na]$^{·+}$, 9.82), 1349.8 ([M+H-1-C$_{21}$H$_{31}$N$_2$O$_{12}$]$^{·+}$, 9.82), 527.2 ([M+H—C$_{66}$H$_{101}$N$_4$O$_{25}$+Na]$^{·+}$, 5.73), 503.4 ([M+H—C$^{66}$H$_{101}$N$_4$O$_{25}$]$^{108\,+}$, 2.54)] confirmed the structure assigned for the desilylated tris-coupled peracylated galactose conjugate.

EXAMPLE 21

Fluoride-promoted Desilylation of Tris-coupled Peracylated Lactose Conjugate

The tris-conjugated peracylated lactose conjugate (Example 19) was desilylated using the procedures of Example 20. The desilylated tris-coupled peracylated lactose conjugate was obtained in 37% yield. Some product overlapped with 20% of starting material and with appreciably more deacetylated by-products (~25%. The $^1$H-NMR of the product (middle spot) in DMSO-d$_6$ was very sharp and several protons were assigned in conjunction with the 2D-COSY spectrum.

The 500 MHZ $^1$ H-NMR and 2D-COSY spectrum showed three carbamate NH's that appeared as broad multiplets between 6.59 and 6.84 ppm. Between 5.09 and 5.33 ppm, three complex multiplets integrated for 12 protons. After evaluation of the 2D-COSY spectra for this area the signals were assigned to three sets of H1' [glucose], H4' [peracylated galactose], H3'[glucose] and H3'[peracylated galactose]. The H2' peracylated galactose proton appeared as an apparent doublet of doublets at 4.83 ppm. The 24-OH group appeared between 3.28 and 3.33 ppm as a very intense broad singlet which overlapped with residual water. The t-butyl and phenyl group H's were absent. From $^{13}$C-NMR and 2D-Heteronuclear Multiple Quantum Coherent (HMQC) spectra, many carbons were assigned within the carbohydrate and linker regions. The three anomeric glucose carbons were at 76.50, 76.52 and 76.55 ppm. The peracylated lactose anomeric carbons were at 99.80, 99.77 and 99.70 ppm. The 24-CH$_2$OH carbon was at 61.17 ppm. The above NMR data and the electrospray mass analysis [(DMF/AcOH) m/z: 2740.1 ([M+Na]$^+$, 100.0), 2756.1 ([M+K]$^+$, 11.8)] confirmed the structure assigned for the desilylated tris-coupled peracylated lactose conjugate.

EXAMPLE 22

Dimethoxytrityl Tetraol

The desilylation of the tris-coupled peracylated lactose conjugate using the above TBAF method was more problematic than for the galactosyl conjugate probably because of the higher bulkiness and the possible increased hindrance of the TBDPS group rendering it inaccessible to fluoride ion attack at low TBAF concentrations. To eliminate the restrictions associated with this route another method was used to synthesize the tris-coupled peracylated lactose conjugate.

Tetraol (prepared in Example 15) was reacted with 1.1 eq. of dimethoxytrityl chloride (DMT-Cl) in the presence of 0.1 eq. of DMAP in dry pyridine at 0° C. After 10 minutes the reaction mixture was allowed to warm to room temperature. The reaction was allowed to proceed for 6 hours and the crude material obtained after workup was purified by silica gel column chromatography to give the title compound in a 64% yield.

The methylene protons at position 24 (—CH$_2$O-DMT) appeared as a multiplet between 2.86 and 2.94 ppm in the $^1$H-NMR spectrum. The 7- and 12-equatorial —CH(OH)— appeared as singlets at 3.59 and 3.76 ppm, respectively. The 3-axial —CH(OH)— appeared as a multiplet between 3.14 and 3.19 ppm. The two methoxy CH$_3$ appeared as a sharp singlet at 3.71 ppm and the phenyl protons appeared between 6.8 and 7.3 ppm. The NMR data and the mass spectrum {FAB-NBA m/e 697 [M+H]$^+$; 303 [M+H-(C$_{24}$H$_{41}$O$_4$)]$^+$, 100} confirmed the assigned structure.

EXAMPLE 23

Synthesis of DMT-protected Tris-NHS Cholane Derivative, DMT-protected Active Ester Dimethoxytrityl tetraol was reacted with triphosgene (2 eq.) in dry pyridine at 0° C. After 15 minutes at 0° C., N-hydroxysuccinimide (NHS, 10 eq.) was added. The reaction mixture became cloudy and thickened. Within 10 minutes the mixture started to become light red and at 15 minutes the reaction mixture was poured into cold water. The ester precipitated out of the solution and after drying, the active ester was obtained in 89% yield.

The 3-,7- and 12-α-CH protons appeared at 4.55–4.61 (multiplet), 4.87 (singlet) and 5.03 (singlet) ppm in the $^1$H-NMR spectrum. The downfield shift of all the α-CH and the multiplet at 2.78–2.83 ppm, corresponding to the 12 succimidyl methylene protons [—(O)C—CH$_2$CH$_2$C(O)—] confirmed the tris activation. The NMR data and the mass spectrum [(FAB-NBA) m/e: 1143.38 ([M+Na]$^+$, 0.4), 1120.47 ([M+H]$^+$, 1.1), 303.21 ([M+H—C$_{39}$H$_{50}$N$_3$O$_4$]$^+$, 100)] confirmed the assigned structure.

EXAMPLE 24

Preparation of DMT-protected Lactosylated Conjugate

The DMT-active ester was reacted with lactosylamine (3.3 eq.) in dry DMF at room temperature. After 120 hours, the reaction mixture was poured into ice water and the a 1:1 mixture of tritylated and detritylated tris-coupled peracylated lactose conjugate was obtained in >80% yield. The observed detritylation was not problematic since the following step was the trifluoroacetic acid treatment (detritylation). A small amount of the mixture was subjected to column chromatography and the two spots were separated and individually characterized by NMR and electrospray mass spectrometry. The remainder of the mixture was completely detritylated in the following step.

EXAMPLE 25

Cleavage of the DMT-group with Trichloroacetic Acid (TCA)

The mixture of protected and deprotected tris substituted peracylated lactose conjugates (Example 23) was reacted with 6% TCA in dry CH$_2$Cl$_2$ at room temperature. The reaction mixture was quenched with methanol and triethylamine after 1.5 hours. Flash column chromatography using a increasingly polar eluent mixture (CH$_2$Cl$_2$ to 2.5% MeOH/CH$_2$Cl$_2$ to 5% MeOH/CH$_2$Cl$_2$) gave the deblocked tris peracylated lactose conjugate in 80% yield. Electrospray MS and NMR were identical to those reported for the tris peracylated lactose conjugate previously obtained in Example 21 using the TBAF method. Using the DMT protection scheme, 500 mg of pure tris peracylated lactose conjugate was prepared as required for biological testing.

EXAMPLE 26

General Method of Incorporating Tris-coupled Peracylated Galactose Conjugate (Example 20) into an Oligonucleotide or an Oligonucleoside The tris-coupled peracylated galactose conjugate of Example 20 is activated with disuccinimidyl carbonate (DSC, Fluka) to give the carbamate derivative. The carbamate is then treated with 4-amino-2-hydroxy butanol (prepared as per J. Am. Chem. Soc. 109, 3089., 1987) to give the corresponding carbamate. The primary alcohol function is then treated with dimethoxytrityl chloride/pyridine to give the DMT derivative.

The DMT derivative is then phosphitylated using 2-cyanoethyl-N,N-diisopropylchlorophosphoramidite in the presence of diisopropyl ethyl amine in methylene chloride as the solvent. The resulting DMT phosphoramidite derivatized tris-coupled peracylated galactose conjugate is incorporated at the terminal 5'-OH or 3'-OH of an oligonucleotide or an oligonucleoside.

Alternatively the DMT phosphoramidite is coupled to a free 5'-OH position of a nucleotide, nucleoside, oligonucleotide or an oligonucleoside. Followed by deblocking of the DMT group the free primary hydroxyl is available for coupling to a further nucleotide, nucleoside, oligonucleotide or an oligonucleoside to effect incorporation of the conjugate at an internal position.

EXAMPLE 27

Incorporation of Tris-coupled Peracylated Lactose Conjugate (Example 21) into an Oligonucleotide or an Oligonucleoside Both the DMT and DMT phosphoramidite tris-coupled peracylated lactose conjugate (Example 21) are prepared as per the procedure illustrated in Example 26. The DMT phosphoramidite is further incorporated onto the 3' or 5' position or at an internal position of an oligonucleotide or an oligonucleoside.

EXAMPLE 28

General Method, Attachment of the DMT-tris-coupled Peracylated Galactose Conjugate (Example 26) onto Solid Support DMT-tris-coupled peracylated lactose conjugate (Example 26) is succinylated using succinic anhydride (1.5 equivalents), triethylamine (1 equivalent), 4-dimethylamino pyrimidine (0.5 equivalent) in anhydrous 1,2-dichloroethane at 50° C. (as per the procedure of Kumar et al., *Nucleosides and Nucleotides,* 1993, 12, 565–584). After workup the resulting succinate is dried under vacuum at room temperature. The succinate is then condensed with controlled pore glass that has been pre-acid washed (CPG Inc., New Jersey) (as per the procedure of Bayer et al., *Z. Naturforsch,* 1995, 50b, 1096–1100). The amino-functionalized CPG is suspended in anhydrous DMF and treated with 1 equivalent of the succinate, 1 equivalent of TBTU (2-(1H-benzotriazole-1-yl)-1,1,3,3-tetra-methyluronium tetra-fluoroborate) and 2 equivalents of N-methyl morpholine (NMM). After 12 hours of shaking the functionalized CPG, support is filtered and washed with DMF, methylene chloride and methanol. The final rinse is carried out with ether and the derivatized solid support is obtained after drying under vacuum.

EXAMPLE 29

Attachment of the DMT-tris-coupled Peracylated Lactose Conjugate (Example 27) onto Solid Support The DMT protected tris-coupled peracylated lactose conjugate (Example 27) is attached to a solid support as per the procedures illustrated in Example 28.

EXAMPLE 30

Preparation of Tetra-coupled Cyclohexanone Peracylated Carbohydrate Conjugate

Cyclohexanone is treated with base (KOH) followed by four equivalents of acrylonitrile. The resultant tetracyano compound is subjected to a Witting reaction (—C=O to —C—CH$_2$) followed by hydroboration to convert the olefin to a primary alcohol. Catalytic hydrogenation with Pd/H$_2$ to convert the cyano groups to methylamino groups will give the tetra-aminopropyl-cyclohexylhydroxymethyl compound having 4 linker groups attaching 4 amino groups. The tetra-aminopropyl-cyclohexylhydroxymethyl compound is then condensed with carbohydrate groups using either a reductive amination route (e.g., acylated lactose) or isocyanate condensation to give the tetra-carbohydrate substituted-aminopropyl-cyclohexylhydroxymethyl compound. The free hydroxyl group is extended with a linker such as 4-amino-2-hydroxy-butanol in a similar manner as illustrated above in Example 26. Introduction of the primary and secondary hydroxyl groups enables the preparation of the DMT or DMT phosphoramidite conjugates. The conjugates can be incorporated internally or at the 3' or 5' terminus of a nucleotide, nucleoside, oligonucleotide or an oligonucleoside as illustrated in Example 26 above.

EXAMPLE 31

Preparation of Tetra-coupled-5-aminoisophthalic Acid Conjugate

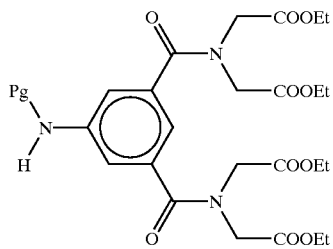

The above compound prepared as per the procedure of Hayashi et al., *J. Am. Chem. Soc.,* 1998, 120, 4910–4915) is treated with HBr/HOAC and condensed with pentafluorophenyl ester of TBDPS-O—(CH$_2$)$_6$—COOH (Pg=TBDPS). The resulting tetraester is refluxed with KOH/THF/MeOH to give tetracarboxylic acid compound. Either of the carbohydrate derivatives prepared in Examples 9 and 10 are condensed with the tetracarboxylic acid compound above using TBTU/NMM to give the tetra-sugar conjugated compound. The silyl protecting group is removed by treatment with tBuN$^+$F$^-$ and the alcohol is phosphitylated to give the conjugate phosphoramidite. The conjugate phosphoramidite is used to conjugate the carbohydrate cluster to an oligonucleotide or an oligonucleoside as illustrated in Example 26 above.

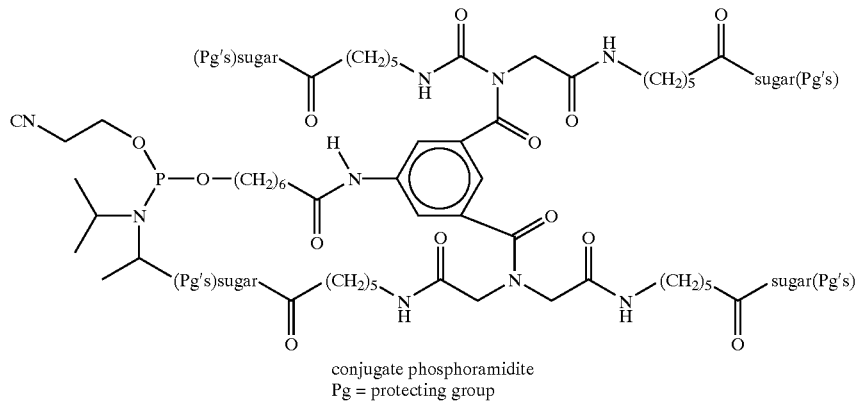

conjugate phosphoramidite
Pg = protecting group

Alternatively, the free hydroxyl obtained after removal of the TBDPS group can be activated using an activating agent followed by treatment with a linker group having one functionality to couple with the conjugate group and also having a primary and a secondary hydroxyl group. Introduction of the primary and secondary hydroxyl groups enables the preparation of the DMT or DMT phosphoramidite conjugates. The conjugates can be incorporated internally or at the 3' or 5' terminus of a nucleotide, nucleoside, oligonucleotide or an oligonucleoside as illustrated in Example 26 above.

What is claimed is:

1. A method of facilitating cellular uptake of a primary moiety comprising:
    identifying a cell surface receptor on a target cell; and
    contacting said cell with a complex, said complex comprising:
        at least two cell surface receptor ligands; and
        a manifold covalently connected to said primary moiety and to each of said cell receptor ligands, wherein said manifold is a polycyclic molecule.

2. The method of claim 1 wherein said primary moiety is a nucleoside, nucleotide, oligonucleoside, oligonucleotide or pro-drug form of said nucleoside, nucleotide, oligonucleoside or oligonucleotide.

3. The method of claim 1 wherein said complex comprises at least three cell surface receptor ligands which are the same.

4. The method of claim 1 wherein said complex has from three to four cell surface receptor ligands which are the same.

5. The method of claim 1 wherein said primary moiety is selected as a peptide, protein, a molecule that can bind RNA, an antibiotic compound or an antibacterial compound.

6. The method of claim 1 wherein said polycyclic molecule comprises an aliphatic ring system, an aromatic ring system, a heterocyclic ring system, a mixed ring system having two or more aliphatic aromatic or a plurality of heterocyclic ring connected or fused,
    wherein said complex has a plurality of reactive sites thereon.

7. The method of claim 1 wherein said manifold comprises cholic acid or a cholic acid derivative.

8. The method of claim 1 wherein said cell surface receptor ligands are carbohydrates.

9. The method of claim 8 wherein said carbohydrates are mono- or polysaccharides.

10. The method of claim 9 wherein said saccharides are galactose, lactose, N-acetylgalactosamine, mannose or mannose 6-phosphate.

11. The method of claim 1 wherein said cell surface receptor ligands are galactose or lactose.

12. A method of facilitating cellular uptake of a primary moiety comprising:
    identifying a cell surface receptor on a target cell; and
    contacting said cell with a complex, said complex having the formula:

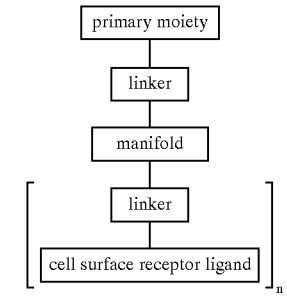

wherein
    said primary moiety is a nucleoside, nucleotide, oligonucleoside,oligonucleotide, or a pro-drug form of said nucleoside, nucleotide, oligonucleoside or oligonucleotide;
    each of said linkers are, independently, bi- or trifunctional;
    said manifold is derivatized at a plurality of sites, said manifold being a polycyclic molecule;
    each of said cell surface receptor ligands is a carbohydrate; and
    n is from 2 to about 8.

13. The method of claim 12 wherein there are at least three copies of the same cell surface receptor ligand.

14. The method of claim 12 wherein said primary moiety is a peptide, protein, a molecule that can bind RNA, an antibiotic or an antibacterial compound.

15. The method of claim 12 wherein said polycyclic molecule comprises an aliphatic ring system, an aromatic ring system, a heterocyclic ring system, a mixed ring system having two or more aliphatic aromatic and heterocyclic rings connected or fused, wherein said complex optionally has a plurality of reactive sites thereon.

16. The method of claim 12 wherein said manifold is cholic acid or a cholic acid derivative.

17. The method of claim 12 wherein said cell surface receptor ligands are carbohydrates.

18. The method of claim 17 wherein said carbohydrates are independently mono- or polysaccharides.

19. The method of claim 18 wherein said saccharides are, independently, galactose, lactose, N-acetylgalactosamine, mannose or mannose 6-phosphate.

20. The method of claim 12 wherein said cell surface receptor ligands are galactose or lactose.

21. The method of claim 12 wherein n is from 2 to 6.

22. The method of claim 12 wherein n is from 2 to 4.

* * * * *

UNITED STATES PATENT AND TRADEMARK OFFICE
CERTIFICATE OF CORRECTION

PATENT NO. : 6,525,031 B2
DATED : February 25, 2003
INVENTOR(S) : Muthiah Manoharan It is certified that error appears in the above-identified patent and that said Letters Patent is hereby corrected as shown below:

Title page,
Item [56], References Cited, OTHER PUBLICATIONS,
"Agrawal", reference, please delete "olidogeoxynucleoside" and insert therfor
-- Oligodeoxynucleoside -- ;
"Azad", reference, please delete "Phsophorothioate" and insert therefor
-- Phosphorothioate -- ;
"Bayer", reference, please delete "Soldi" and insert therefor -- Solid -- ;
"Bayer", reference, please delete "50B" and insert therefor -- 50b -- ;
"Betebenner", reference, please delete "witn" and insert therfor -- with -- ,
"Bevicacqua, reference , please replace "Molecular" with -- Molecule -- ;
"Birchenall-Roberts", reference, please delete "inhibiton" and insert therefor
-- inhibition -- ;
"Birchenall-Roberts, reference, please delete "Factro-1" and insert therefor
-- Factor-1 -- ;
"Boutorin", reference, please delete "oligonucletide" and insert therefor
-- oligonucleotide -- ;
"Boutorin",  reference, please delete "3+-terminus" and insert therfor -- 3'-terminus --
"Drickamer-4", reference, please delete "Glycoprotien" and insert therefor
-- Glycoprotein -- ;
"Letsinger", reference, please delete "Synthsis" and insert therfor -- Synthesis -- ;
"Letsinger", reference please delete "inhibiors" and insert therefor -- inhibitors --;
"Molema", reference, please delete "Moleman" and insert therfor -- Molema -- ;
"Zerial", reference, please delete "infleunza" and insert therfor  -- influenza --.

Signed and Sealed this

Twenty-ninth Day of June, 2004

JON W. DUDAS
*Acting Director of the United States Patent and Trademark Office*